(12) United States Patent
Sinko et al.

(10) Patent No.: US 9,763,968 B2
(45) Date of Patent: *Sep. 19, 2017

(54) HYDROGEL FORMULATION FOR DERMAL AND OCULAR DELIVERY

(71) Applicant: Rutgers, The State University of New Jersey, New Brunswick, NJ (US)

(72) Inventors: Patrick J. Sinko, Lebanon, NJ (US); Manjeet Deshmukh, Edison, NJ (US); Siva N. Priya Anumolu, Edison, NJ (US); Anupa R. Menjoge, Highland Park, NJ (US); Marion K. Gordon, Princeton, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/168,542

(22) Filed: May 31, 2016

(65) Prior Publication Data

US 2016/0271151 A1    Sep. 22, 2016

Related U.S. Application Data

(60) Continuation-in-part of application No. 14/968,041, filed on Dec. 14, 2015, which is a continuation of application No. 12/450,995, filed as application No. PCT/US2008/005246 on Apr. 23, 2008, now Pat. No. 9,211,358, application No. 15/168,542, which is a continuation-in-part of application No. 14/656,361, filed on Mar. 12, 2015, which is a division of application No. 14/453,968, filed on Aug. 7, 2014, now abandoned, which is a continuation of application No. 13/879,440, filed as application No. PCT/US2010/053566 on Oct. 21, 2010, now abandoned, said application No. 14/453,968 is a division of application No. 11/793,566, filed as application No. PCT/US2005/046891 on Dec. 22, 2005, now abandoned.

(60) Provisional application No. 60/925,910, filed on Apr. 24, 2007, provisional application No. 61/393,653, filed on Oct. 15, 2010, provisional application No. 60/638,552, filed on Dec. 22, 2004.

(51) Int. Cl.

| | |
|---|---|
| A61K 31/65 | (2006.01) |
| A61K 9/00 | (2006.01) |
| A61K 47/10 | (2017.01) |
| A61K 9/06 | (2006.01) |
| A61K 47/34 | (2017.01) |
| A61K 47/48 | (2006.01) |
| A61K 33/40 | (2006.01) |

(52) U.S. Cl.
CPC ............ *A61K 31/65* (2013.01); *A61K 9/0014* (2013.01); *A61K 9/0048* (2013.01); *A61K 9/0051* (2013.01); *A61K 9/06* (2013.01); *A61K 33/40* (2013.01); *A61K 47/10* (2013.01); *A61K 47/34* (2013.01); *A61K 47/48215* (2013.01); *A61K 47/48238* (2013.01); *A61K 47/48784* (2013.01)

(58) Field of Classification Search
CPC .... A61K 31/65; A61K 9/0014; A61K 9/0048; A61K 47/10; A61K 9/06; A61K 47/48238; A61K 47/48784; A61K 9/0051; A61K 47/48215; A61K 33/40; A61K 47/34

See application file for complete search history.

(56) References Cited

U.S. PATENT DOCUMENTS

| 4,681,582 | A | 7/1987 | Yamamoto |
| 5,631,018 | A | 5/1997 | Zalipsky et al. |
| 5,853,755 | A | 12/1998 | Foldvari |
| 6,051,648 | A | 4/2000 | Rhee et al. |
| 6,312,720 | B1 | 11/2001 | Katinger et al. |
| 6,475,516 | B2 | 11/2002 | DiCosmo et al. |
| 6,740,335 | B1 | 5/2004 | Moynihan et al. |
| 7,104,894 | B2 | 9/2006 | Bennett |
| 9,211,358 | B2 * | 12/2015 | Sinko .................. A61L 26/0076 |
| 2002/0122785 | A1 | 9/2002 | Stein et al. |
| 2006/0134226 | A1 * | 6/2006 | Leonard ............... A61K 31/047 |
| | | | 424/638 |

FOREIGN PATENT DOCUMENTS

| CN | 101564374 A | 10/2009 |
| EP | 0088642 | 9/1983 |
| EP | 0056962 | 10/1985 |
| EP | 0325247 | 5/1993 |
| EP | 0296612 | 6/1994 |
| EP | 0540099 | 4/1996 |
| EP | 0321122 | 9/1996 |

(Continued)

OTHER PUBLICATIONS

Emerson et al., "In Vivo Antitumor Activity of Two New Seven-substituted Water-Soluble Camplothecin Analogues," Canc Res, 1995, vol. 55, No. 3, pp. 603-609 (Abstract only).

(Continued)

*Primary Examiner* — Suzanne Ziska
(74) *Attorney, Agent, or Firm* — Fox Rothschild LLP

(57) ABSTRACT

Formulations of cross-linkable polymers, capable of forming non-toxic and biocompatible hydrogels in situ, containing at least one of doxycycline or minocycline. Methods of using the hydrogels for treating the skin or ocular tissues of mammals exposed to vesicant compounds such as sulfur mustard (SM), nitrogen mustard (NM) or half mustard (2-chloroethyl ethyl sulfide (CEES)) are also disclosed.

15 Claims, 20 Drawing Sheets

(56) References Cited

FOREIGN PATENT DOCUMENTS

| EP | 0737686 | | 7/1999 |
|---|---|---|---|
| WO | 90/03169 | | 4/1990 |
| WO | 96/37496 | | 11/1996 |
| WO | 96/38146 | | 12/1996 |
| WO | 96/38449 | | 12/1996 |
| WO | 97/00876 | | 1/1997 |
| WO | 2008/005276 | * | 1/2008 |

OTHER PUBLICATIONS

Gregoriadis, "Immunological adjuvants: A role for liposomes," Immunol Today, 1990, vol. 11, pp. 89-97 (Abstract only).
Liposome Technology, 2nd ed. 1993, vol. 1, p. 157.
Canc. Research, 1997, vol. 38, Abst. 1526 or 95. (Sandiego Apr. 12-16).
Maeda, AFMC Int. Med. Chem. Symp. 1997, PB-55 (Seoul, Jul. 27-Aug. 1).
Suffness et al., The Alkaloids Chemistry and Pharmacology Bross ed., vol. 25, p. 73, Academic Press, 1985.
Qui et al., "A hydrogel prepared by in situ cross-linking of a thiol-containing poly(ethylene glysol)-based copolymer: a new biomaterial for protein drug delivery," Biomaterials, vol. 24, pp. 11-18.
Information about Related Patents and Patent Applications, see section 6 of the accompanying Information Disclosure Statement Letter, which concerns Related Patents and Patent Applications.
International Search Report issued in Application No. PCT/US2005/046891 dated Jun. 19, 2006.
International Preliminary Report on Patentability issued in Application No. PCT/US2005/046891 dated Jun. 26, 2007.

* cited by examiner

SEQUENCE LISTING

<160> NUMBER OF SEQ ID NOS: 8

<210> SEQ ID NO 1
<211> LENGTH: 11
<212> TYPE: PRT
<213> ORGANISM: Artificial

-continued

```
<220> FEATURE:
<223> OTHER INFORMATION: Synthetic DV3 peptide

<400> SEQUENCE: 1

Leu Gly Ala Ser Trp His Arg Pro Asp Lys Cys
1               5                   10

<210> SEQ ID NO 2
<211> LENGTH: 9
<212> TYPE: PRT
<213> ORGANISM: Artificial
<220> FEATURE:
<223> OTHER INFORMATION: Synthetic LYP peptide

<400> SEQUENCE: 2

Cys Gly Asn Lys Arg Thr Arg Gly Cys
1               5

<210> SEQ ID NO 3
<211> LENGTH: 14
<212> TYPE: PRT
<213> ORGANISM: Artificial
<220> FEATURE:
<223> OTHER INFORMATION: Synthetic IGFBP3 membrane binding domain

<400> SEQUENCE: 3

Gln Cys Arg Pro Ser Lys Gly Arg Lys Arg Gly Phe Cys Trp
1               5                   10

<210> SEQ ID NO 4
<211> LENGTH: 5
<212> TYPE: PRT
<213> ORGANISM: Artificial
<220> FEATURE:
<223> OTHER INFORMATION: Synthetic peptide

<400> SEQUENCE: 4

Glu Leu Gly Leu Gly
1               5

<210> SEQ ID NO 5
<211> LENGTH: 4
<212> TYPE: PRT
<213> ORGANISM: Artificial
<220> FEATURE:
<223> OTHER INFORMATION: Synthetic peptide

<400> SEQUENCE: 5

Arg Gly Asp Cys
1

<210> SEQ ID NO 6
<211> LENGTH: 5
<212> TYPE: PRT
<213> ORGANISM: Artificial
<220> FEATURE:
<223> OTHER INFORMATION: Synthetic peptide

<400> SEQUENCE: 6

Gly Arg Gly Asp Ser
1               5

<210> SEQ ID NO 7
<211> LENGTH: 6
<212> TYPE: PRT
<213> ORGANISM: Artificial
<220> FEATURE:
```

-continued

```
<223> OTHER INFORMATION: Synthetic peptide

<400> SEQUENCE: 7

Gly Arg Gly Asp Ser Pro
1               5

<210> SEQ ID NO 8
<211> LENGTH: 5
<212> TYPE: PRT
<213> ORGANISM: Artificial
<220> FEATURE:
<223> OTHER INFORMATION: Synthetic peptide

<400> SEQUENCE: 8

Arg Gly Asp Tyr Lys
1               5
```

HYDROGEL FORMULATION FOR DERMAL AND OCULAR DELIVERY

The present application is a continuation application of U.S. application Ser. No. 13/879,440, filed on Aug. 23, 2013, which is a U.S. National Phase of International Patent Application Serial No. PCT/US10/53566, filed on Oct. 21, 2010, which claims priority benefit under 35 U.S.C. §119(e) of U.S. Provisional Patent Application Ser. No. 61/393,653, filed Oct. 15, 2010. This present application is also a continuation-in-part application of U.S. application Ser. No. 14/656,361, filed on Mar. 12, 2015, which is a divisional application of U.S. application Ser. No. 14/453,968, filed on Aug. 7, 2014, which is a divisional application of U.S. application Ser. No. 11/793,566, filed on Jan. 24, 2008, which is a U.S. National Phase of International Patent Application Serial No. PCT/US05/46891, filed on Dec. 22, 2005, which claims priority benefit under 35 U.S.C. §119(e) of U.S. Provisional Patent Application Ser. No. 60/638,552, filed on Dec. 22, 2004. The disclosures of which are incorporated herein by reference in their entireties.

STATEMENT REGARDING FEDERALLY FUNDED RESEARCH

This invention was made with government support under Grant U54AR055073 awarded by the National Institute of Arthritis and Musculoskeletal and Skin Diseases. Accordingly, the U.S. Government has certain rights in this invention.

BACKGROUND OF THE INVENTION

Field of the Invention

The present invention relates to compositions of polyalkylene oxide hydrogels, as well as methods of making and using the hydrogel for wound healing applications. More particularly, embodiments relate to compositions comprising functionalized polyethylene glycol (PEG) in new and useful configuration hydrogels.

Description of the Related Art

Vesicants such as sulfur mustard, nitrogen mustard and half mustard are potent cytotoxic and mutagenic agents. Sulfur mustard (SM) has the chemical formula bis(2-chloroethyl) sulfide and is a well known chemical warfare agent. It was first used as such during World War I and has been subsequently used in over 10 additional conflicts.

Nitrogen mustard and half mustard are analog derivatives of SM and, just like SM, also have potential as chemical warfare agents. Half mustard (CEES) has the chemical formula 2-chloroethyl ethyl sulfide, and nitrogen mustard (NM) encompasses a class of chloroalkyl amines, the three most common species including bis(2-chloroethyl) ethyl amine (HN1); bis(2-chloroethyl) methyl amine (HN2) and tris(2-chloroethyl) amine (HN3). Many countries have been stockpiling these derivatives for use as chemical warfare agents, but none have ever been used.

The toxicity between SM, NM and CEES varies. Nevertheless, exposure to any one of these agents can cause devastating injuries to the eyes, skin and respiratory system, with the eyes being the most sensitive tissue to exposure. SM, for example, exhibits a threshold in the eyes of 12 mg·min/m$^3$, as compared to 200 mg·min/m$^3$ for the skin. Thus, even low doses of SM, NM, or CEES induce incapacitation, visual impairment and panic. While the molecular mechanisms for SM, NM, or CEES induced injury are unclear, these all exhibit DNA, RNA and protein alkylation and cause inflammation, tissue damage and cell death.

MMPs are a family of enzymes that enhance the action of many activating factors during inflammatory response and contribute to tissue degradation. MMP-9 has been identified as a potential target of therapy for SM, NM, and/or CEES damage since it was found that its expression and activation quantitatively increases over time in response to SM exposure. The cornea is clinically impaired by such exposure exhibiting chronic inflammation and increased MMP activity. Decreased MMP-9 activity in humans has been found to correlate with accelerated wound healing. Hence, intervention targeting of both the inflammatory response and increased protease expression could provide a therapeutic approach for the treatment of vesicant induced corneal wounds.

Doxycycline is a long acting semi-synthetic tetracycline analog, which is well recognized for its therapeutic efficacy in treating MMP mediated ocular surface diseases, such as rosacea, recurrent epithelial erosions and sterile corneal ulcerations. Doxycycline has been found to inhibit MMP-9 activity in vivo in the corneal epithelial cells of experimental dry eye as well as in vitro in human corneal epithelial cells. Treatment with doxycycline has been shown to be beneficial in attenuating acute and delayed ocular injuries caused by SM exposure. The drug is an inexpensive, FDA approved antibiotic that likely promotes wound healing by reducing inflammation and protease activity.

Minocycline is also a long acting semi-synthetic tetracycline analog that exhibits neuroprotective, anti-apoptotic, and anti-inflammatory effects. Recently, it has been shown to inhibit macrophage inflammation and T cell activation, as well as inhibiting the inflammatory effects of the enzyme 5-lipoxygenase. Much like doxycycline, minocycline also has been shown to inhibit MMP-9 activity in vivo, particularly after cerebral ischemia. It has been previously suggested that this MMP inhibitory action could be a central link for minocycline's neuroprotective, anti-apoptotic, and anti-inflammatory effects. For at least this reason, minocycline is also a good candidate for promoting wound healing.

The blood-ocular barriers, which include the blood-aqueous and blood-retina barriers protect the eye, but prevent drug distribution to the anterior and posterior chambers, limiting ocular bioavailability. Drug diffusion into the eyes from the systemic circulation is slow and inefficient. Most drugs applied to the eye surface as solutions have ocular bioavailability in the range of about 10% with most of the drug being cleared by local systemic absorption. Solutions are in contact with the eye surface for a very short period of time as the tear film quickly washes them away.

The contact time, local drug concentration and thereby duration of action can be prolonged by designing topical formulations with higher viscosities. The ideal drug delivery system for corneal wound repair should be nontoxic, transparent, easy to administer, possess rheological properties to maintain its structural integrity, provide a microbial barrier, release the drug in a controlled and sustained manner and decrease the time of wound healing. There are very few controlled drug delivery systems reported for corneal wound repair applications. Although doxycycline and minocycline are commercially available in a wide variety of dosage formulations including tablets, capsules and suspensions, topical ocular doxycycline eye drop formulations are to this day compounded by a pharmacist. Since there are currently no ocular formulations commercially available for doxycycline, there is a critical need for a controlled release doxycycline delivery system that can be easily applied to the eye to promote wound healing.

SUMMARY OF THE INVENTION

The instant invention addresses these and other needs by providing, in one aspect, a formulation comprising a cross-linkable polymer capable of forming non-toxic and biocompatible hydrogels in situ and at least one of doxycycline or minocycline. In certain embodiments, the formulation is adapted for topical or ocular administration. Preferably, though not exclusively, the formulation is administered in a liquid form and forms a hydrogel in situ.

In certain embodiments, the cross-linkable polymer of the instant formulation is a linear or branched PEG having 2-8 arms, and preferably having a molecular weight of 1000-100,000 Da. The polymer of the instant invention may be derivatized with reactive groups such as, for example, —SH, —NH$_2$, —COOH, or any combination thereof.

In certain embodiments of the invention, the formulation also comprises a cross-linker, wherein the ratio of polymer to the cross-linker is from about 0.05:10 to about 10:0.05, and, more preferably, between 1:1 and 1:2. In different embodiments, the cross-linker may be selected from thiopyridine (TP), N-Hydroxysuccinimide (NHS), vinylsulfone, maleimide, BM[PEO]$_3$-(1,8-bis-maleimido-tri-ethyleneglycol), BM[PEO]$_4$-(1,11-bis-maleimido-triethylene-glycol), BMH-(bis-maleimido-hexane) or BMOE-(bis-maleimidoethane) and combinations thereof.

In other embodiments, the polymer is self-crosslinkable upon reaction with an oxidizing agent such as, without limitation, hydrogen peroxide.

According to any of the embodiments of the instant invention, the concentration of said at least one of doxycycline or minocycline is 0.1-12% (w/v). In certain embodiments, the at least one of doxycycline or minocycline is unmodified. In other embodiments, the at least one of doxycycline or minocycline is coupled to the polymer through degradable bonds. In different embodiments, the degradable bonds are enzyme-sensitive peptide linker bonds, self-immolative linker bonds, acid and base-sensitive linker bonds, pH sensitive linker bonds, multifunctional organic linking agent bonds, multifunctional inorganic crosslinking agent bonds and peptidic backbone bonds.

In some embodiments the at least one of doxycycline or minocycline is bound to a targeting moiety, such as, for example, an RGD peptide, EGF peptide, DV3 peptide (LGASWHRPDKC) (SEQ ID NO: 1), LYP peptide (CGNKRTRGC) (SEQ ID NO: 2), membrane-binding domain of IGFBP3 (QCRPSKGRKRGFCW) (SEQ ID NO: 3), fMLF, mannose, transferrin ligand or monoclonal antibodies. While not limited thereto, in one embodiment the doxycycline or minocycline is bounded by at least one of its hydroxyl residues.

While the foregoing exemplifies in situ administration, in alternative embodiments, particularly with respect to ocular administration, the hydrogel may be provided in a prepared dosage form adapted for release of the active agent in accordance with the foregoing. In one aspect, an ocular dosage form includes the hydrogel fabricated as a contact lens having the active ingredient (e.g. doxycycline or minocycline). Such a dosage form may also include additional excipients or ingredients for such purposes, as defined herein or otherwise known in the art. The prepared dosage forms of the instant invention are not limited to a contact lens and may also be adapted for alternative uses, as generally understood in the art.

In another aspect, the invention provides a method of treating the skin or eyes of a mammal exposed to a vesicant compound by administering to the mammal a formulation according to any of the embodiments of the instantly claimed formulation. In certain embodiments, the vesicant compound is sulfur mustard (SM), nitrogen mustard (NM) or half mustard (2-chloroethyl ethyl sulfide (CEES)). In certain embodiments, the formulation is administered in the form of an ocular formulation to an eye of the mammal. In other embodiments, the formulation is administered in the form of a topical formulation to a portion of the mammal's skin exposed to the vesicant compound.

DETAILED DESCRIPTION OF THE PREFERRED EMBODIMENTS

Definitions

Figure 1:
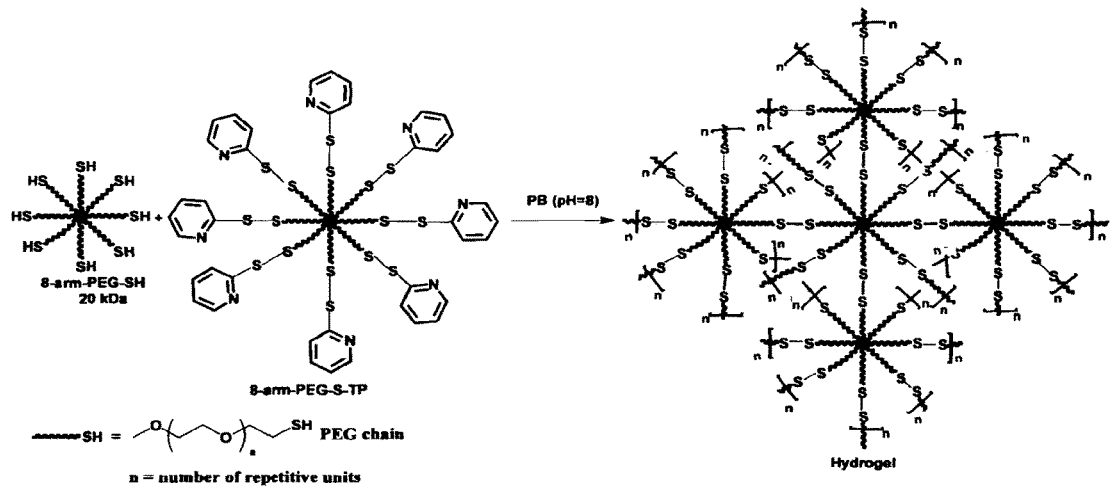
FIG. 1 is an illustration of hydrogel preparation scheme in which a hydrogel is formed using multi-arm thiol-containing PEG with multi-arm PEG cross-linker containing S-TP.

Unless characterized otherwise, technical and scientific terms used herein have the same meaning as commonly understood by one of ordinary skill in the art to which this invention belongs. For purposes of the present invention, the following terms are described below.

"PEG" is used herein as an abbreviation for polyethylene glycol. PEGs are included within the broader class of polyalkylene oxides, which include PEG as well as polypropylene glycols and polyglycol copolymers. PEG can have a range of molecular weights. The PEG molecular weight range contemplated for use in the present invention is from about 1000 to about 100,000 Da. PEG can be linear, branched, multi-arm, or a combination of branched and multi-arm. Various PEGs can be derivatized with various groups, such as activated ester (N-hydroxy succinimide ester), p-nitrophenyl, aldehyde, amine, thiol, activated thiol (thio-pyridine activated thiol, for example), vinyl sulfone, malcimide, aminooxy, hydrazine, tosyl, and idoacetamide.

"Surface modification" includes chemical treatment of nanogel particles or aggregated nanogel particles (ANPs) to modify, for example, the surface charge/charge density, hydrophobicity/hydrophilicity, or both. The actual chemical treatment can be performed on the final material, such as the nanogel particle, or ANP, or it be performed on a precursor material, such as the scaffold or nanocarrier.

"Agent" includes without limitation any therapeutic, palliative, cosmetic and/or prophylactic compositions, including without limitation small molecules, drugs, biologicals, recombinant peptides, proteins and nucleic acids and immunochemicals, as well as diagnostic and imaging compositions, as may be further indicated by the context. In some uses, the term can relate to other types of compositions, as indicated by the context.

Solubility Terms

Unless indicated otherwise, either expressly or by implication, the following solubility terms are used as described in Table 1 below (reproduced from Stegemann et al., "When Poor Solubility Becomes an Issue: From Early Stage to Proof of Concept," Eur. J. Pharm. Sci., 31, 250 (2007)).

TABLE 1

Solubility definition in the USP

| Description forms (solubility definition) | Parts of solvent required for one part of solute | Solubility range (mg/ml) | Solubility assigned (mg/ml) |
|---|---|---|---|
| Very soluble (VS) | <1 | >1000 | 1000 |
| Freely soluble (FS) | From 1 to 10 | 100-1000 | 100 |
| Soluble | From 10 to 30 | 33-100 | 33 |
| Sparingly soluble (SPS) | From 30 to 100 | 10-33 | 10 |
| Slightly soluble (SS) | From 100 to 1000 | 1-10 | 1 |
| Very slightly soluble (VSS) | From 1000 to 10,000 | 0.1-1 | 0.1 |
| Practically insoluble (PI) | >10,000 | <0.1 | 0.01 |

The instant invention addresses the needs of the prior art by providing in one aspect a composition suitable for ocular or topical administration and comprising a cross-linkable, polymer-based hydrogel and an active agent entrapped therein.

The hydrogels evaluated in the current study are formed in situ, in other words, they are liquids upon instillation and undergo a phase transition at physiological pH to form the hydrogel. This occurs by covalent intermolecular crosslinking of polymer chains through reversible thioester bonds, resulting in biodegradable viscoelastic hydrogels. In the current invention, doxycycline/minocycline loaded fast forming PEG hydrogels were designed for the treatment of simulated mustard injuries using CEES, NM and SM vesicants and evaluated in exposed rabbit corneas or on the skin ion the back of the mice or rats.

There are many variations, all of which are considered embodiments of the invention, of the general scheme for hydrogel preparation. One such embodiment as shown in the FIG. 1 uses multi-arm thiol-containing PEG with multi-arm PEG cross-linkers containing S-TP. Upon mixing the multi-arm PEG with the multifunctional cross-linker under proper conditions of pH, reagent concentrations and temperature, covalent bonds are formed due to the reaction of the thiol group with the S-TP. Other bi-functional or multifunctional cross-linkers such as NHS, vinylsulfone or maleimide groups can be used to form the gel upon mixing with a multi-arm PEG thiol. The transition from a liquid to a hydrogel will occur when the network of inter-molecularly crosslinked PEG molecules reaches a particular molecular weight, which depends on many factors. In this embodiment, the cross-linker contains both the chemo-selective group needed for hydrogel formation and an oxidizing agent that oxidizes thiol groups present on the polymers or copolymers. The present invention is directed, in part, to materials and methods for the preparation and use of hydrogels incorporating chemistries allowing for timed degradation and/or release of active agents, which may be embedded therein by covalent or non-covalent means.

Hydrogels (polymer/copolymer, cross-linker, and/or active agents) can be applied to wounded or CEES, NM and SM exposed skin or eyes as a solution, where it is converted into the hydrogel in situ due to the intermolecular crosslinking of polymer/copolymer/cross-linker chains. The hydrogel stays in the applied space and provide controlled-release of active agents (e.g., doxycycline, minocycline, etc.)

Preferably, the polymer comprises at least two thiol groups, and may be a homopolymer or a copolymer.

The hydrogels of the present invention include at least one cross-linkable polymer, which is cross-linked to entrap the therapeutic agent, which is may be encapsulated, for example, within a liposome. Any cross-linkable polymer bearing two or more functional or reactive groups capable of participating in a cross-linking reaction to form a matrix of the invention may be used. Such functional groups include but are not limited to amino, carboxyl, thiol and hydroxyl groups, or combinations thereof; and reactive groups include vinylsulfone, maleimide, pyridyldithio and other moieties capable of reacting with the aforementioned functional groups, among others.

A preferred polymer is one on which at least two thiol groups are present and is cross-linked with a thiol-reactive bi-functional cross-linking reagent in the presence of the encapsulated therapeutic agent, thus forming a cross-linked polymer with the liposome encapsulated therapeutic agent physically entrapped therein. Selection of the appropriate polymer, the concentration in the matrix, the extent of functional groups capable of participating in cross-linking, the type of cross-linking agent, and the extent of cross-linking, and other factors may be governed by the amount of liposome encapsulated therapeutic agent present in the composition in order to achieve the desired controlled release properties of the composition, or retention of the liposomes within the composition.

Examples of suitable polymers for the preparation of the polymer on which at least two thiol groups are present include either homopolymers or copolymers. By way of non-limiting example, suitable polymers, which may be chemically modified to comprise thiol groups, include poly-alkylene oxides such as poly(ethylene glycol) [also known as poly-ethylene glycol or PEG, polyethylene oxide or PEO], carboxymethylcellulose, dextran, poly-vinyl alcohol, N-(2-hydroxypropyl)methacrylamide, polyvinyl pyrrolidone, poly-1,3-dioxo-lane, poly-1,3,6-trioxane, polypropylene oxide, a copolymer of ethylene/maleic anhydride, a polylactide/polyglycolide copolymer, a polyaminoacid, a copolymer of poly(ethylene glycol) and an amino acid, or a polypropylene oxide/ethylene oxide copolymer.

Such polymers are then derivatized or further polymerized to introduce thiol groups, and chemical modification of the polymer may be necessary as a step prior to the further derivatization to incorporate thiol groups. In certain embodiments, for example, a polymer of the present invention may be derived from a poly(ethylene glycol) (PEG) derivative, for example, $\alpha,\omega$-dihydroxy-PEG or $\alpha,\omega$-diamino-PEG, but other derivatives are embraced herein. In certain embodiments the polymer comprising thiol groups may be, for example, a polymer of $\alpha,\omega$-diamino-poly(ethylene glycol) and thiomalic acid; a polymer of $\alpha,\omega$-dihydroxy poly(ethylene glycol) and thiomalic acid; or a polymer of $\alpha,\omega$-dicarboxy-PEG subunits and lysine, wherein the free carboxy groups on the lysine residues are derivatized to form thiol groups.

These polymers are only examples of possible choices, as the skilled artisan will be aware of numerous alternatives. The selection of the polymer, or combinations thereof, may be guided by the desired properties of the final product such as, for example, the duration of release of the therapeutic agent and the release kinetics. In certain embodiments, a product of the invention may comprise more than one polymer component in order to provide two or more different release characteristics. In certain embodiments, more than one therapeutic agent may be included.

In certain preferred embodiments, a polymer of the present invention is derived from a poly(ethylene glycol) (PEG) derivative, for example, $\alpha,\omega$-dihydroxy-PEG or $\alpha,\omega$-diamino-PEG, but other derivatives are embraced herein. Examples of such polymers with particular molecular weights include $\alpha,\omega$-dihydroxy-$PEG_{3,400}$; $\alpha,\omega$-dihydroxy-$PEG_{1,000}$; $\alpha,\omega$-diamino-$PEG_{3,400}$ and $\alpha,\omega$-diamino-$PEG_{1,000}$. PEG is known to be a particularly nontoxic polymer. These derivatized PEG subunit polymers may be used as amino- and hydroxy-containing polymers for cross-linking, or may be further derivatized, for example, to prepare the polymer on which at least two thiol groups are present by derivatization with thiomalic acid. Thio-malic acid (also known as mercaptosuccinic acid) may be replaced by dimercaptosuccinic acid, thereby doubling the number of sites available for cross-linking. Increasing the extent of cross-Linking the matrix results in a gel with smaller pores and thus regulates the rate of release of the active agent.

In certain embodiments, the cross-linking can be performed before, during, or after the matrix is administered to a mammal. For example, the cross-linking reaction can be initiated in vitro, and the mixture, while undergoing cross-linking, may administered to a mammal, wherein the administered composition continues to cross-link and harden in situ. In certain embodiments, a cross-linked matrix after formation can be administered.

In certain embodiments, the polymer moieties may be cross-linked by reagents capable of forming covalent bonds between the functional groups, such as but not limited to homobifunctional and heterobifunctional cross-linking agents. As described above, one preferred moiety is a thiol group. In certain embodiments, a preferred cross-linking agent is one that forms thioether bonds, such as a vinylsulfone or maleimide, but the invention is not so limiting. Other cross-linking reagents, such as a pyridyldithio-containing reagent, or oxidation, may be used to generate reducible cross-links. Combinations of cross-linking reagents may be used, to provide a ratio of cross-link types, which generate the desired release characteristics of the composition. In certain embodiments, the preferred thiol-containing polymer has from 2 to about 20 thiol groups, preferably from about 3 to about 20 thiol groups, and most preferably from about 3 to about 8 thiol groups. In certain embodiments, the thiol groups on the polymer are sterically hindered.

Various conditions and/or reagents may be used to effect the cross-linking of the polymer, depending on the particular functional groups on the polymer. By way of non-limiting example, the conditions that cause cross-linking of the thiol groups on a thiol-containing polymer may be reaction in the presence of an oxidizing agent or reaction with a cross-linking agent. The oxidizing agent may be by way of non-limiting example, molecular oxygen, hydrogen peroxide, dimethylsulfoxide, and molecular iodine. The cross-linking agent may be a bifunctional disulfide-forming cross-linking agent or a bifunctional thioether-forming cross-linking agent. In a preferred embodiment, the cross-linking agent is a long-chain cross-linking agent, with a molecular weight of about 300 to about 5,000 Da. Non-limiting examples of suitable cross-linking agent include 1,4-di-[3', 2'-pyridyldithio(propion-amido)butane]; $\alpha,\omega$-di-O-pyridyldi-sulfidyl-poly(ethylene glycol); a vinyl sulfone such as $\alpha,\omega$-divinylsulfone-poly(ethylene glycol); 1,11-bis-maleimidotetraethylene glycol; and $\alpha,\omega$-diiodoacetamide-poly(ethylene glycol).

For other functional groups or a combination of a thiol group and another group, any appropriate bi-functional cross-linking agent may be selected which will achieve the desired cross-linking of the functional groups and formation of the cross-linked polymer.

In certain embodiments, the release rate of the therapeutic or other agent in the composition of the invention may be regulated by the biodegradability of the cross-linked polymer matrix, the liposome or combination thereof. In certain embodiments, the degradation rate may be adjusted by varying the ratio or types of cross-links of the matrix, and the stability or lability thereof, in the composition. For example, the ratio of reducing agent-sensitive disulfide bonds, esterase-sensitive ester bonds, and stable thioether bonds may be selected to provide the desired release kinetics of the active agent. In certain embodiments, the release rate is adjusted by adjusting the pore size of the pores in the hydrogel matrix.

In certain embodiments, the polymer is PEG-based (i.e., comprises more than 50% w/w of PEG which may be straight or branched). The hydrogel is based on intermolecular cross-linking of soluble PEG polymers, which form an insoluble, high molecular weight PEG hydrogel matrix. Active agents may be loaded into this hydrogel prior to the cross-linking reaction, so that the hydrogel will serve as a depot for the sustained release of that agent. The chemical reaction used for forming the hydrogel by cross-linking polymer and cross-linker. Non-limiting examples of methods to accomplish this includes: (i) using chemo-selective pairs of reactive groups, for example, the cross-linker may comprise a thiol-reactive group such as vinylsulfone or maleimide, S-TP or NHS that will react with thiol groups on PEG; and (ii) using oxidizing agents like $H_2O_2$ for the cross-linking reaction.

General Procedure for Hydrogel Formation

Hydrogels are formed in situ by reaction between a multivalent copolymer or PEG polymer and cross-linker in aqueous medium. Several combinations are possible: (i) the PEG polymer or copolymer contain thiol groups whereas the cross-linker has thiol-reactive S-TP, NHS, vinylsulfone, maleimide etc. groups; or (ii) the polymer or copolymer containing thiol groups cross-linked with oxidizing agents like $H_2O_2$ etc. The hydrogels disclosed herein can be obtained over a broad concentration range of the polymers or copolymers, and cross-linkers. The concentration ranges of the polymer or copolymer is 1%-20% (w/v) and that of the cross-linker is 1%-15% (w/v). The ratios of the polymer or copolymer to the cross-linker in the hydrogel vary from 0.05:10 to 10:0.05 and preferably between 1:1 and 1:2. Either single type of polymer/copolymer and cross-linker is used or a combination of different types of unmodified and modified copolymer or polymer and cross-linkers is used.

The formulation of the instant invention may be prepared by reacting a PEG-SH or PEG-COOH having from 2 to 8 arms and a molecular weight from about 1 to 20 kDa with cross-linkers comprising S-TP and/or NHS in DMF to obtain PEG-AA-S-TP or PEG-AA-NHS, wherein AA is derived from the cross-linker and is selected from GABA (gamma-amino butyric acid); AHA (6-aminohexanoic acid), AOA (8-aminooctanoic acid), GABA-GABA, AHA-AHA, AOA-AOA, AHA-GABA, AOA-GABA, AHA-GAA and combinations thereof.

Polymers for Hydrogel Formation.

Linear or multi-arm (2 to 8) PEGs contain multiple thiol groups within a molecular weight range of 1000-100,000 Da. Polymers can be unmodified or modified with active agents (timed-release mechanism, other degradation mechanism, or degradation preventing mechanisms) prior to hydrogel formation.

Copolymer Containing Thiol Groups.

The invention can be extended to copolymers containing repeating units of thiol groups. For example, copolymer like poly[poly(ethylene glycol)-alt-poly (mercaptosuccinic acid)] in the molecular weight range of 10,000 to 100,000 Da. Copolymers can also be unmodified or modified with active agents (timed-release mechanism, other degradation mechanism, or degradation-preventing mechanism) prior to hydrogel formation.

Polymer Containing Peptide Thiol Groups.

The invention can be extended to polymers containing repeating units of peptide thiol groups such as polycysteine in the molecular weight range of 1,000 to 100,000 Da. These polymers can also be unmodified or modified with active agents prior to hydrogel formation.

Cross-Linkers for Hydrogel Formation.

Cross-linkers containing functional groups like S-TP, NHS, vinyl sulfone and maleimide groups or thiol groups are used for hydrogel formation through thioether or disulfide bonds. Cross-linkers can be linear or branched and contain 2-8 functional groups, with molecular weights in the range of 1-20 kDa.

Cross-Linkers Containing Vinylsulfone Groups.

The cross-linkers containing terminal vinylsulfone (VS) functional groups like 1,6-Hexane-bis-vinylsulfone (HBVS) can also be used.

Cross-Linkers Containing Maleimide Groups (MA).

Cross-linkers containing terminal maleimide groups like BM[PEO]$_3$-(1,8-bis-maleimidotriethyleneglycol) or BM[PEO]$_4$-(1,11-bis-maleimidotriethyleneglycol) or BMH-(bis-maleimidohexane) or BMOE (bis-baleimidoethane) can also be used.

Cross-Linkers Containing Thiol Groups.

Thiol-containing cross-linkers such as dithiothreitol, polycysteines, PEG-thiol's or 4-arm thiol, 8-arm thiol can be used.

Active Agents.

In certain embodiments, the active agent includes doxycycline and/or minocycline. The instant invention is not limited to the forgoing may include one or a combination of any of the following active agents: anti-inflammatory drugs, doxycycline, minocycline, NSAID analogs, NSAID-ache (NSAID-acetylcholin-esterase complexes, steroidal anti-inflammatory drugs, anti-cancer drugs, HIV protease inhibitors, monoclonal antibodies, imaging agents, and combinations thereof. In certain other embodiments, the agent is selected from one or more of the following: indomethacin, sancycline, a sancycline analog, olvanil, an olvanil analog, retro-olvanil, a retro-olvanil analog, olvanil carbamate, budesonide, a budesonide analog, methylprednisolone, a methylprednisolone analog, dexamethasone, a dexamethasone analog, camptothecin, carboplatin, doxorubicin, paclitaxel, saquinavir mesylate, amprenavir, ritonavir, indinavir, nelfinavir mesylate, tipranavir, darunavir, atazanavir sulfate, a coloring dye, an FD and C dye, a visible/near infrared fluorescence dye, fluorescein, methylene blue, rhodamine, dansyl, Alexa, a cyanine dye, Hilyte, indocyanine green, and combinations thereof. More preferably, the agent is doxorubicin.

For passive entrapment, the agent may be unmodified or coupled to the PEG through degradable bonds (prodrugs) like enzyme-sensitive peptide linkers, self-immolative linkers, acid and base-sensitive linkers, pH sensitive linkers, multifunctional organic linking agents, multifunctional inorganic crosslinking agents and/or peptidic backbones represented as:

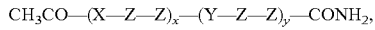

where X=Lys, Glu, Asp or diaminobutyric acid; Y=Cys, homocysteine or 1-amino-2-methyl-2-propanethiol; Z=β-Ala, Gly, Ala, or GABA (gamma-amino butyric acid); x and y are interchangeable; x is between 1 to 4; y is between 1 to 4; minimum number of Z-spacer on the peptide backbone=2; maximum number of Z-spacer on the peptide backbone=4.

In variations, the active agent may further comprise a targeting moiety. The targeting moiety may be a peptide, and preferably such a peptide is an RGD peptide. In certain other embodiments, the targeting group is selected from an RGD peptide, EGF peptide, DV3 (LGASWHRPDKC) (SEQ ID NO: 1) peptide, a LYP peptide (CGNKRTRGC) (SEQ ID NO: 2), a membrane-binding domain of IGFBP3 (QCRPSK-GRKRGFCW) (SEQ ID NO: 3), fMLF, mannose, transferrin ligand and monoclonal anti-bodies. When the drug is doxycycline, the linker used may also be any of following: Leu-Gly, Glu(Leu-Glyh (SEQ ID NO: 4), Arg-Gly-Asp-Cys (SEQ ID NO: 5), Gly-Arg-Gly-Asp-Ser (SEQ ID NO: 6), Gly-Arg-Gly-Asp-Ser-Pro (SEQ ID NO: 7), cyclic ArgGly-Asp-Tyr-Lys (SEQ ID NO: 8) or any peptide with Arg-Gly-Asp. While not limiting to the invention, in such embodiments, doxycycline and/or minocycline may be linked to targeting moieties or linkers by any of its hydroxyl groups.

In variations, the active agent may contain a targeting unit selected from the targeting groups listed above.

Either for passive entrapment or timed release, a single active agent can be used or combinations of active agents can be used, and the active agent content in the hydrogel formulation may vary from 0.1-12% (w/v). Thus, in different embodiments, the active agent content is 1%, 2%, 3%, 4%, 5%, 6%, 7%, 8%, 9%, 10%, 11%.

In certain embodiments, the timed release of the active agent is from about 1 minute to about 1440 h. In certain embodiments, the timed release of the active agent is from about 1 min to about 720 h. In certain embodiments, the timed release of the active agent is from about 1 min to about 490 h. In certain embodiments, the timed release of the active agent is from about 1 min to about 360 h. In certain embodiments, the timed release of the active agent is from about 1 min to about 119 h. In certain embodiments, the timed release of the active agent is from about 1 min to about 96 h. In certain embodiments, the timed release of the active agent is from about 1 min to about 72 h. In certain embodiments, the timed release of the active agent is from about 1 min to about 48 h. In certain embodiments, the timed release of the active agent is from about 1 min to about 24 h. In certain embodiments, the timed release of the active agent is from about 1 min to about 12 h. In certain embodiments, the timed release of the active agent is from about 1 min to about 6 h.

The general procedure for release of active agents from hydrogels preferably involves the following processes:

(i) Passive entrapment and release. In one embodiment, the active agent(s) are physically entrapped into the hydrogel by mixing it in the formulation (polymer/copolymer and cross-linker) prior to hydrogel formation. In alternative embodiments, the agent(s) may be incorporated into a second phase (e.g. nanoparticle, microparticle, or the like) and passively dispersed in the hydrogel. The active agent content in the hydrogel formulation may vary from 0.1-12% (w/v) and the formulation may contain one active agent or a combination of active agents.

(ii) Active entrapment and release. In other embodiments, the active agent(s) may be covalently attached into the hydrogel by and releasable as provided herein.

While the foregoing exemplifies in situ administration, in alternative embodiments, particularly with respect to ocular administration, the hydrogel may be provided in a prepared dosage form adapted for release of the active agent in accordance with the foregoing. In one aspect, the ocular dosage form includes a contact lens fabricated, at least in part, from the active ingredient (e.g. doxycycline or minocycline) containing hydrogel of the instant invention. Such a dosage form may also include additional excipients or ingredients for such a purposes. To this end, the contact lens may be comprised entirely of the active agent-containing hydrogel in accordance with the foregoing. Alternatively, it may be comprised of a combination of the foregoing hydrogel with one or more additional hydrogels, polymers, or other components known in the art for use in preparing a hard or soft contact lens. In either embodiment, the contact lens is adapted to be fully or partially biodegradable such that the lens releases the active agent over a period of time. The prepared dosage forms of the instant invention are not limited to a contact lens and may also be adapted for alternative uses in accordance with the teaching herein and as generally understood in the art.

The invention is described more fully by way of the following non-limiting examples. All references cited above and hereafter in this document are hereby incorporated by reference in their entirety herein.

EXAMPLES

Example 1—Preparation of Doxycycline hydrogel using 8 Arm PEG-SH and 8 Arm PEG NHS A. Preparation of Sodium Phosphate Buffer (0.1 M, pH 8.00±0.05)

A solution of sodium phosphate dibasic (1 M, Catalog # S-9763, Sigma Aldrich, St. Louis, Mo.) was prepared in a volumetric flask by dissolving 14.2 grams of salt in 100 mL of deionized (DI) water. Similarly, the solution of sodium phosphate monobasic (1M, Catalog # S-0751, Sigma Aldrich, St. Louis, Mo.) was prepared in another flask by dissolving 12.0 grams of salt in 100 mL DI water. 9.32 mL of sodium phosphate dibasic and 0.68 ml of sodium phosphate monobasic solutions were transferred to a beaker. DI water (80.0 mL) was added to the beaker and the pH of the solution was measured as described in example 3A. The pH was adjusted to 8.00 using 0.1 N sodium hydroxide solution (Catalog # SS276-4, Fisher Scientific, Suwanee, Ga.). The buffer was transferred to a volumetric flask and DI water was added to adjust the final buffer volume to 100 mL. Unless otherwise indicated, all reference to DI refers to deionized water. Likewise, unless otherwise indicated, all reference to PB in examples refers to 0.1 M phosphate buffer, pH, 8.00.

B. Preparation of Cross-Linker Solution 8-arm $PEG_{20kDa}$-$[NHS]_8$ (10 mg, Catalog # SUNBRIGHT PTE-200GS, NOF America Corporation, White Plains, N.Y.) was weighed in a centrifuge tube and dissolved in PB (100 μL). The Doxycycline (0.6 mg) was added to this solution and vortexed (<1 minutes) to make a clear solution.

C. Preparation of Polymer Solution Containing the Nano-carrier 8-arm $PEG_{20kDa}$-$[SH]_8$ (Hexa-glycerine, octa-(thioethylene)poly(ethylene glycol) ether)) (5 mg, Catalog # SUNBRIGHT PTE-200SH, NOF America Corporation, White Plains, N.Y.) was weighed in a centrifuge tube and dissolved in PB (100 μL) by vortexing for <1 minutes.

D. Preparation of Hydrogel (0.2 mL)

The cross-linker solution (100 μL) containing the nano-carrier was transferred to a glass vial (12×32 mm, SepCap clear vial, Catalog # C4011-80, National Scientific Company, Rockwood, Tenn.) followed by the polymer solution (100 μL). The solution mixture was allowed to stand at room temperature (24° C.). The hydrogel solution started becoming more and more viscous after 30 Sec and ceased to flow from the inverted tube in 48 Sec indicating the formation of hydrogel.

Hydrogel examples with passively entrapped drugs are summarized in Table 2.

TABLE 2

| Cross-linker | Polymer | Nanocarrier | Polymer/cross-linker composition | Time for hydrogel formation |
|---|---|---|---|---|
| $PEG_{20\,kDa}$-$[NHS]_8$ | $PEG_{20\,kDa}$-$[SH]_8$ | Doxycycline | 1:2 (10 and 20% w/v) | 60 minutes |
| $PEG_{40\,kDa}$-$[NHS]_8$* | $PEG_{20\,kDa}$-$[SH]_8$ | Doxycycline | 1:1 (5% w/v) | 90 minutes |
| $PEG_{20\,kDa}$-$[NHS]_8$* | $PEG_{20\,kDa}$-$[SH]_8$ | Doxycycline | 1:1 (7.5% w/v) | 85 minutes |
| $PEG_{40\,kDa}$-$[NHS]_8$* | $PEG_{20\,kDa}$-$[SH]_8$ | Doxycycline | 1:2 (5 and 10% w/v) | 75 minutes |
| $PEG_{20\,kDa}$-$[NHS]_8$ | $PEG_{20\,kDa}$-$[SH]_8$ | Doxycycline | 1:1 (10% w/v) | 65 minutes |
| $PEG_{40\,kDa}$-$[NHS]_8$* | $PEG_{20\,kDa}$-$[SH]_8$ | Doxycycline | 1:1 (15% w/v) | 55 minutes |
| $PEG_{40\,kDa}$-$[NHS]_8$* | $PEG_{20\,kDa}$-$[SH]_8$ | Doxycycline | 1:2 (15 and 30% w/v) | 30 minutes |

*Hydrogels prepared using the procedure described in example 1.

Example 2—Preparation of Doxycycline Hydrogels Using 8 Arm PEG-SH ($H_2O_2$)

Phosphate buffer is prepared as in example 1.

A. Preparation of Polymer Solution 8-arm $PEG_{20kDa}$-$[SH]_8$ (4 mg, Catalog # SUNBRIGHT PTE-200SH, NOF America Corporation, White Plains, N.Y.) was weighed in a centrifuge tube and dissolved in PB (100 μL) by vortexing for <1 minutes.

B. Preparation of Hydrogel (0.2 mL)

The polymer solution (100 μL) containing the nanocarrier was transferred to a glass vial (12×32 mm, SepCap clear vial, Catalog # C4011-80, National Scientific Company, Rockwood, Tenn.) followed by $H_2O_2$ solution (1.9 μL) was added into the polymer solution. The solution mixture was allowed to stand at room temperature (24° C.). The hydrogel solution started becoming more and more viscous after 40 Sec and ceased to flow from the inverted tube in 78 Sec indicating the formation of hydrogel.

Hydrogel examples with passively entrapped drugs are summarized in Table 3.

TABLE 3

| Polymer (% w/v) | Nanocarrier | $H_2O_2$ volume (μl) | Total wt of polymers (% w/v) | Time for hydrogel formation |
|---|---|---|---|---|
| $PEG_{20\,kDa}$-$[SH]_8$ (4%) | Doxycycline | 1.9 | 4 | 75 minutes |
| $PEG_{40\,kDa}$-$[SH]_8$*(8%) | Doxycycline | 5.4 | 8 | 55 minutes |

*Hydrogels prepared using the procedure described in example 2.

Example 3—Preparation of Minocycline Hydrogel Using 8 Arm PEG-SH and 8 Arm PEG NHS Phosphate buffer is prepared as in example 1.

A. Preparation of Polymer Solution 8-arm $PEG_{20kDa}$-$[SH]_8$ (10 mg, Catalog # SUNBRIGHT PTE-200SH, NOF America Corporation, White Plains, N.Y.) was weighed in a centrifuge tube and dissolved in PB (100 μL) by vortexing for <1 minutes.

B. Preparation of Cross-Linker Solution Containing the Nanocarrier 8-arm $PEG_{20kDa}$-$[NHS]_8$ (10 mg, Catalog # SUNBRIGHT PTE-200GS, NOF America Corporation, White Plains, N.Y.) was weighed in a centrifuge tube and dissolved in PB (100 μL). The Minocycline (0.6 mg,) was added to this solution and vortexed (<1 minutes) to make a clear solution.

C. Preparation of Hydrogel (0.2 mL)

The cross-linker solution (100 μL) containing the nanocarrier was transferred to a glass vial (12×32 mm, SepCap clear vial, Catalog # C4011-80, National Scientific Company, Rockwood, Tenn.) followed by the polymer solution (100 μL). The solution mixture was allowed to stand at room temperature (24° C.). The hydrogel solution started becoming more and more viscous after 30 Sec and ceased to flow from the inverted tube in 48 Sec indicating the formation of hydrogel.

Hydrogel examples with passively entrapped drugs are summarized in Table 4.

TABLE 4

| Cross-linker | Polymer | Nanocarrier | Polymer to cross-linker ratio | Time for hydrogel formation |
|---|---|---|---|---|
| $PEG_{20\,kDa}$-$[NHS]_8$ | $PEG_{20\,kDa}$-$[SH]_8$ | Minocycline | 1:2 | 48 Sec. |

Example 4—Preparation of Minocycline Hydrogels Using 8 Arm PEG-SH and 8 Arm PEG TP Phosphate buffer and polymer solutions, were prepared as in example 1.

A. Preparation of Cross-Linker Solution Containing the Nanocarrier 8-arm $PEG_{20}kDa$-$[TP]_8$ (10 mg) was weighed in a centrifuge tube and dissolved in PB (100 μL)). The Doxycycline (0.6 mg,) was added to this solution and vortexed (<1 minutes) to make a clear solution.

B. Preparation of Hydrogel (0.2 mL)

The cross-linker solution (100 μL) containing the nanocarrier was transferred to a glass vial (12×32 mm, SepCap clear vial, Catalog # C4011-80, National Scientific Company, Rockwood, Tenn.) followed by the polymer solution (100 μL). The solution mixture was allowed to stand at room temperature (24° C.). The hydrogel solution started becoming more and more viscous after 30 Sec and ceased to flow from the inverted tube in 48 Sec indicating the formation of hydrogel.

Hydrogel examples with passively entrapped drugs are summarized in Table 5.

TABLE 5

| Cross-linker (%, w/v) | Polymer (%, w/v) | Nanocarrier | Polymer to cross-linker ratio | Time for hydrogel formation |
|---|---|---|---|---|
| 8 arm-$PEG_{20\,kDa}$-$[NHS]_8$ (5%) | 8 arm-$PEG_{20\,kDa}$-$[SH]_8$ (5%) | Doxycycline | 1:1 | <10 sec. |

TABLE 5-continued

| Cross-linker (%, w/v) | Polymer (%, w/v) | Nanocarrier | Polymer to cross-linker ratio | Time for hydrogel formation |
|---|---|---|---|---|
| 8 arm-PEG$_{20\,kDa}$-[NHS]$_8$* (8%) | 8 arm-PEG$_{20\,kDa}$-[SH]$_8$ (8%) | Doxycycline | 1:1 | <10 sec. |

*Hydrogels prepared using the procedure described in example 4.

Example 5. Optical Transmission Properties of Hydrogels

Phosphate buffer, cross-linker solution, polymers and hydrogels were prepared as it in Example 1.

The hydrogels were screened for their potential application as drug delivery systems for corneal wound repair. Different hydrogel compositions [5% (1:1), 7.5% (1:1); 7.5% (1:2); 10% (1:1); 15% (1:1); 15% (1:2); and 22.5% (1:2)] were analyzed for their Optical transmission (OT) properties. The hydrogels (200 µL) were placed in a quartz cuvette containing distilled water and transmission of light was measured at 480 nm using a UV-Vis spectrophotometer. A cuvette containing only distilled water was used as reference. All OT studies were done in triplicate and the mean SEM reported. One-way analysis of variance (ANOVA) was used to determine the effect of hydrogel composition on its OT. Hydrogels with OT 90% were classified as transparent; those in the 10-90% range were classified as translucent, and those 10% as opaque.

Figure 2:
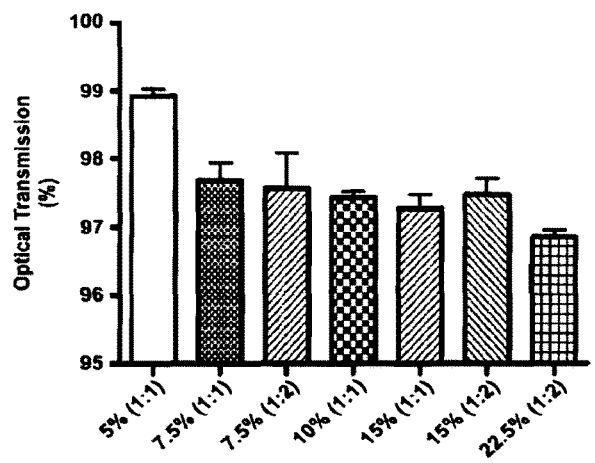
FIG. 2 illustrates optical transmission of 5% (1:1), 7.5% (1:1), 7.5% (1:2), 10% (1:1), 15% (1:2), 15% (1:1), and 22.5% (1:2) hydrogels.

The % OT of various hydrogels is shown in FIG. 2 and as can be seen from the figure, all hydrogels used in this study are transparent. It was also observed that a change in hydrogel composition produces a statistically significant effect (p<0.05) on their OT properties. An increase in the concentration of 8-arm-PEG-SH and/or 8-arm-PEG-NHS resulted into a slight decrease in the transparency of the hydrogels. The transparent characteristic of these hydrogels could be beneficial for their use as ocular drug delivery systems.

Example 6—Rheology of Hydrogels

Phosphate buffer, and cross-linker solution, polymers and hydrogels were prepared as in Example 1.

Figure 3:
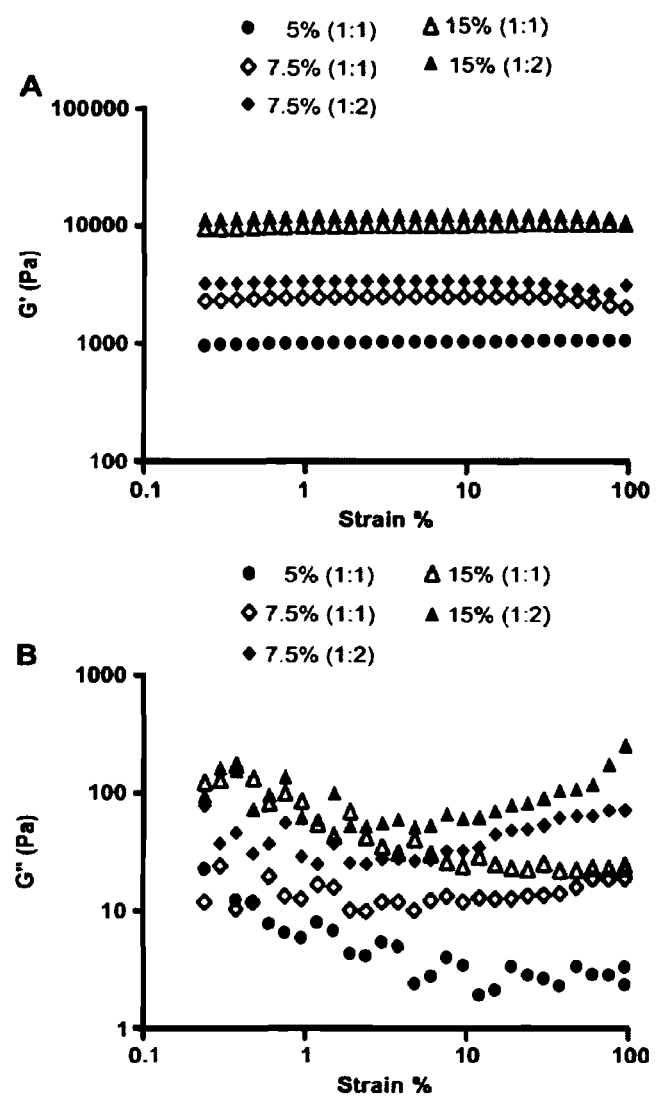
FIG. 3 demonstrates the influence of strain on G' (A) and G" (B) of 5% (1:1), 7.5% (1:1), 7.5% (1:2), 15% (1:1), and 15% (1:2) hydrogels, which depicts the range of linear visco-elasticity for the hydrogels.
Figure 4:
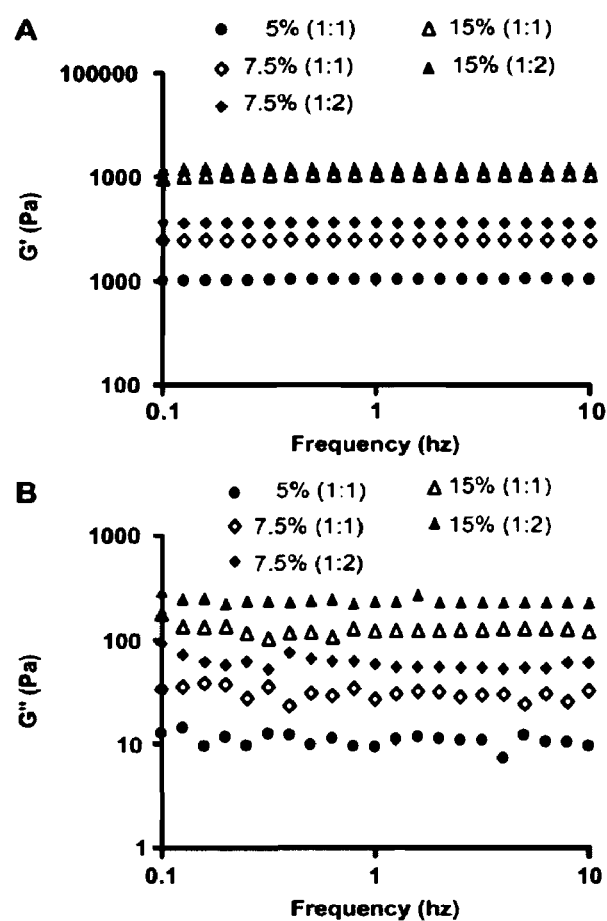
FIG. 4 demonstrates the influence of frequency on G' (A) and G" (B) of 5% (1:1), 7.5% (1:1), 7.5% (1:2), 15% (1:1), and 15% (1:2) hydrogels.

The rheological measurements of hydrogels (prepared in example 1) [5% (1:1), 7.5% (1:1), 7.5% (1:2), 15% (1:1) and 15% (1:2)] were performed using a rheometer with cone plate geometry at 37° C. (plate diameter: 25 mm, gap: 3 mm, 2° angle). The hydrogel samples were equilibrated on the plate for 5 min to reach the running temperature before each measurement. The viscoelastic properties of the hydrogels were evaluated by strain sweep test (FIG. 3) and frequency sweep test (FIG. 4). Both tests are used to obtain the rheological parameters G' (storage/elastic modulus), G" (loss/viscous modulus) and loss tangent/phase angle (tan δ=G"/G'). G' represents the elastic storage of energy and is a measure of how well-structured a hydrogel is. G" represents the viscous energy dissipation and changes depending on the viscosity of the hydrogel.

The strain sweep test results suggest that G' dominates in both the formulations and this is supported by the results obtained from the frequency sweep test. Since G' was one order higher than G", the hydrogels are more elastic than viscous in the investigated frequency range. FIGS. 2 and 3 also show that G' is independent of frequency and strain whereas G" is weakly dependent on both. The hydrogels crosslinked in a 1:2 ratio have slightly higher G' and G" than hydrogels crosslinked in a 1:1 ratio. This can be attributed to the formation of denser and stronger crosslinking networks in 1:2 hydrogels.

A change in hydrogel composition resulted in a statistically significant effect (p<0.001) on the mechanical strength of the hydrogels. The hydrogels containing higher concentrations of polymers [15% (1:1) and (1:2)] showed a higher and constant G' under increasing frequency, suggesting that the hydrogels have the ability to resist structural changes under strain. The small tan δ values indicate that G' is the dominant feature in all the hydrogels and that variations in hydrogel composition do not result in extreme variations in rheological parameters. The rheological data show that the hydrogels have good viscoelastic properties, which might help prolong their ocular residence time and prevent structural break-age. An increased contact time in turn may lead to an increased duration of pharmacological response.

Example 7—Hydrogels Swelling Studies

Phosphate buffer, cross-linker solution, polymers, and hydrogels were prepared as in Example 1.

Figure 5:
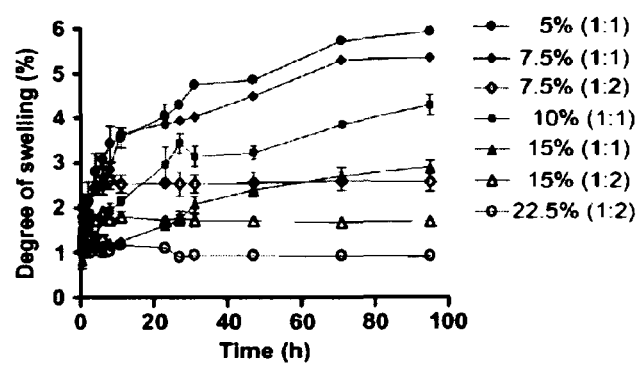
FIG. 5 demonstrates the effect of polymer concentration and crosslinking density on the swelling kinetics of 5% (1:1), 7.5% (1:1), 7.5% (1:2), 10% (1:1), 15% (1:1), 15% (1:2), and 22.5% (1:2) hydrogels.

The degree of swelling for different NHS hydrogels (prepared in example 1) [5% (1:1); 7.5% (1:1); 7.5% (1:2); 10% (1:1); 15% (1:1); 15% (1:2); and 22.5% (1:2)] was measured. Hydrogels were placed in a vial and weighed (initial weight) prior to being immersed in PBS (pH 7.4) and placed in an incubator at 37° C. The degree of swelling of the hydrogels was calculated by weighing the vials after removing the PBS at predetermined time intervals. The buffer was replaced after every measurement and the hydrogels were allowed to swell until equilibrium is reached. FIG. 5 shows the degree of swelling expressed as percent swelling plotted against time for 5% (1:1), 7.5% (1:1), 7.5% (1:2), 10% (1:1), 15% (1:1), 15% (1:2) and 22.5% (1:2) hydrogels. The hydrogels in this study showed a relatively lower degree of swelling (<7%).

The hydrogels crosslinked in a 1:1 ratio initially swelled rapidly, and then gradually reached equilibrium. Furthermore, the hydrogels crosslinked in a 1:2 ratio showed a much lower degree of swelling (<3%) than hydrogels crosslinked in a 1:1 ratio (<7%). A change in hydrogel composition resulted in a statistically significant effect (p<0.001) on the degree of swelling. Hence, a smaller pore size of the hydrogels obtained from increasing the polymer concentration or crosslinking ratio results in a lower degree of hydrogel swelling.

Example 8—Drug Loading Efficiency of Hydrogels

Phosphate buffer, cross-linker solution, polymers, and hydrogels were prepared as in Example 1.

The 10% (1:1), 15% (1:1), 15% (1:2), and 22.5% (1:2) NHS hydrogels (prepared in example 1) loaded with 0.25% w/v of doxycycline were used for drug loading and release studies. The hydrogels were dissected into small pieces and suspended in 5 mL PBS (pH 7.4). The suspension was sonicated for 30 min to completely extract doxycycline from the hydrogel. The amount of doxycycline extracted was quantified by RP HPLC analysis at a wavelength of 350 nm. 0.01M oxalic acid, acetonitrile and methanol (70:18:12) were used as mobile phase at a flow rate of 1 mL/min.

After extraction, suspension containing the hydrogel was stored for several days at 4° C. and then reanalyzed to ensure the complete extraction of doxycycline from the hydrogel. Doxycycline was stable under the storage conditions, as determined by HPLC analysis. Doxycycline loading efficiency results show that 22.5% (1:2), 15% (1:2), 15% (1:1) and 10% (1:1) hydrogels resulted in doxycycline loading efficiencies of 44.7, 47.5, 51.4 and 48.2%, respectively. Higher drug loading efficiency was observed when equivalent ratios of the polymers were used.

Example 9—In Vitro Drug Release from Hydrogels

Phosphate buffer, cross-linker solution, polymers, and hydrogels were prepared as in Example 1.

In vitro release of doxycycline from the NHS hydrogels were studied on a Franz diffusion cell apparatus with a diameter of 5 mm and a diffusion area of 0.636 $cm^2$. A polycarbonate membrane (0.4μ) was sandwiched between the lower cell reservoir and the glass cell-top containing the sample for doxycycline release studies. The receiving compartment (volume 5.1 mL) was filled with PBS (pH 7.4). The system was maintained at 37° C. using a circulating water bath and a jacket surrounding the cell. The receiving medium was continuously stirred (600 rpm) with a magnetic bar to avoid stagnant aqueous diffusion layer effects. 200 μL sample of each hydrogel formulation containing 0.25% w/v doxycycline was prepared and placed in the donor compartment, which was then sealed with parafilm and aluminum foil to prevent evaporation.

Figure 6:
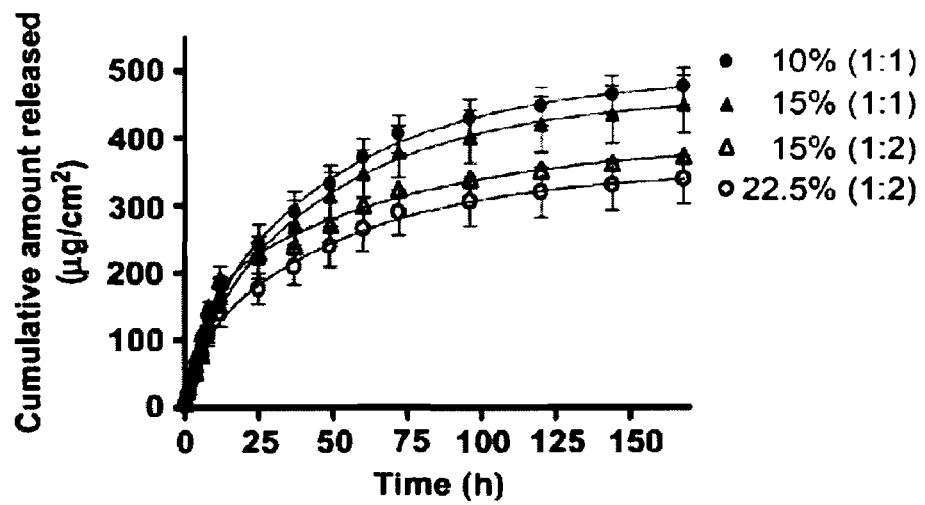
FIG. 6 is an illustration of the cumulative amount of doxycycline released as a function of time for hydrogels: 10% (1:1), 15% (1:2), 15% (1:1), and 22.5% (1:2), with the data fitted using a two-phase exponential association equation in GraphPad Prism 4 software with the fit varying from 0.87 to 0.99.

Aliquots (200 μL) were collected from the receiver compartment at predetermined intervals and replaced with equal volume of PBS to maintain sink conditions throughout the study. The concentration of doxycycline in the release medium was determined using RP HPLC. The cumulative amount of doxycycline released from the hydrogel was determined using a calibration curve. A plot of cumulative amount of doxycycline released (μg/$cm^2$) as a function of time (h) (FIG. 6) demonstrates that doxycycline entrapped in the hydrogel shows sustained drug release for about 7 days (168 h) with 80 to 100% of doxycycline being released from different formulations. From FIG. 5, it appears that as the total concentration of the polymers increased in the hydrogels, the release of doxycycline was sustained. Also, as the crosslinking density increases from 1:1 to 1:2 in the hydrogels, a slower sustained doxycycline release was observed.

Example 10—Treatment of CEES (half mustard, 2-chloroethyl ethyl sulfide) and NM (nitrogen mustard, bis-chloroethyl-methyl-amine) Using Rabbit Corneas A rabbit cornea organ culture model system adapted from Foreman, et al., Exp. Eye. Res., 62(5), 555-564 (1996) was used to evaluate healing after exposure to model vesicants CEES and NM, followed by subsequent treatment with doxycycline drops or doxycycline hydrogels. Rabbit eyes were stored in DMEM (with penicillin, streptomycin, amphotericin B and gentamicin) and transported to the laboratory on ice. Corneas with a surrounding 2 mm scleral rim were dissected from the eye and placed with the epithelial side facing down into spot plates containing a small amount of DMEM to prevent drying of the epithelium. The corneal endothelial concavity was then filled with DMEM containing 0.75% agar at 50° C. and this mixture was allowed to set (usually within 1 min).

Corneas were then inverted and transferred to 60 mm sterile tissue culture dishes and cultured at 37° C. in a humidified 5% $CO_2$ incubator in the presence of medium (500 mL high glucose DMEM, 5 mg ciprofloxacin, 5 mL of 100× MEM-NEAA, 5 mL RPMI 1640 vitamin solution and 50 mg ascorbic acid). To moisten the epithelium, 500 L of medium was added drop wise to the surface of the corneal epithelium every 8 h. The level of medium in dishes was allowed to rise only to the corneal-scleral rim. All agents were added drop wise to the central cornea. Either 200 nmoles CEES (dissolved first in absolute ethanol and then DMEM) or 100 nmoles NM (dissolved first in saline and then DMEM) were applied onto the cornea and allowed to remain there unwashed for 2 h. The 2 h time period approximately simulates the time that would pass before an exposure is recognized (based on the delayed times for tearing and pain) and medical help is secured.

Example 11—Permeation of Doxycycline Through Vesicant Exposed Rabbit's Cornea

Phosphate buffer, cross-linker solution, polymers, and hydrogels were prepared as in Example 1.

Corneas untreated with either of the above vesicants (CEES or NM; example 10) were used as controls. After 2 h, the corneas were placed horizontally on the receptor compartment with the endothelial surface facing the receiver compartment of the Franz diffusion cell set up. The donor half cell was carefully placed on top of the receptor half cell and clamped. 200 L sample of 15% (1:2) hydrogel encapsulating 0.25% w/v doxycycline was placed in the donor compartment. Aliquots (200 μL) were collected from the receiver compartment at predetermined intervals and replaced with equal volume of PBS to maintain sink conditions through out the study. The concentration of doxycycline in the release medium was determined using a RP HPLC as described above. The cumulative amount of doxycycline permeated through the corneas was determined using a calibration curve. All permeation experiments were done in triplicate and the results reported as mean SEM. Two way ANOVA was used to determine the statistical significance of permeation between different treatment groups.

Figure 7:
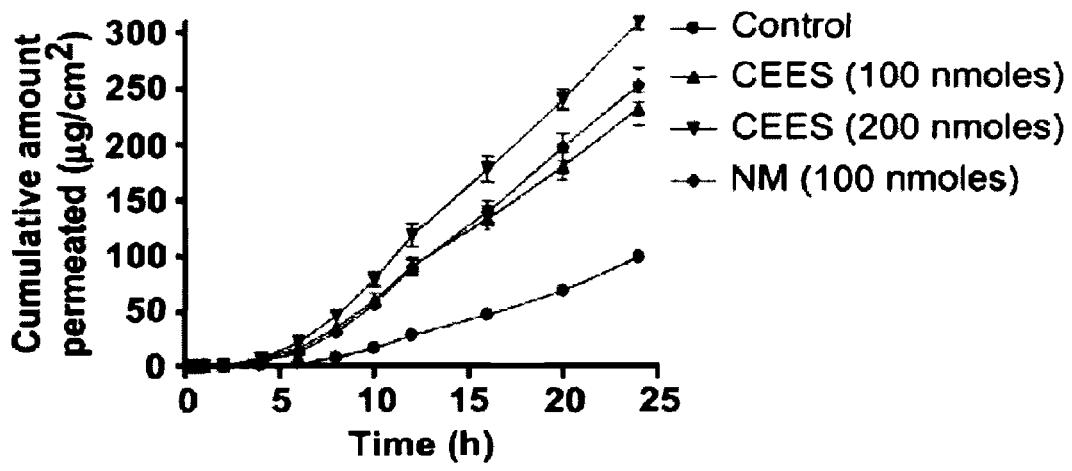
FIG. 7 is an illustration of the cumulative amount of doxycycline permeated as a function of time through cornea exposed to different concentrations of CEES and NM.

The permeation profiles of doxycycline through CEES and NM exposed corneas were evaluated for 24 h using a Franz diffusion cell apparatus. FIG. 7 shows a plot of the cumulative amount of doxycycline permeated (μg/$cm^2$) as a function of time (h). The permeability of doxycycline through CEES and NM exposed corneas was significantly higher than untreated corneas ($p<0.0001$) by 2.5 to 3.3 fold. The cumulative amount of doxycycline permeated through vesicant-exposed corneas is almost equal to the cumulative amount released in 24 h, which verifies that corneal epithelium no longer acts as a barrier for permeation of drugs after exposure.

Example 12—Wound Healing Efficacy of Doxycycline PEG Hydrogels on Corneas Exposed to CEES and NM Phosphate buffer, cross-linker solution, polymers, and hydrogels were prepared as in Example 1.

The CEES or NM-exposed corneas (Example 10) were incubated for 2 h at 37° C.

Medium was replaced with fresh medium after 2 h and then each cornea was treated with doxycycline. Doxycycline solution (2M in 50 μL) was added drop wise to the central cornea 3 times over the subsequent 24 h, whereas 15% (1:2) doxycycline hydrogel (6M in 50 μL) was applied once. After 24 h, the corneas were put in cryomolds containing Tissue-Tek O.C.T. compound with the epithelial side facing down and placed on ice for 15 min before snap freezing them in liquid nitrogen. Corneas were stored at −80° C. until sectioned for histology and immunofluorescence (IF) analysis. The 10 m corneal sections were stained using a modified Hematoxylin & Eosin (H & E) staining method. The corneal sections were fixed in a Pen-Fix solution for 60 s, stained with H & E, dehydrated through graded alcohols, immersed in xylene and covered with a cover slip. Digital images were captured with a light microscope at 40× magnification.

The hydrogel formed a thin transparent film, and likely because of its high water content, the hydrogel was retained in place for the entire duration of the study (24 h). The histology of the control cornea showed an epithelium with normal thickness and an intact stroma with corneal keratocytes separated by extracellular matrix. The controls treated with hydrogel (not shown) and doxycycline hydrogel were very similar to the controls demonstrating that the hydrogel did not cause damage to the cornea. The CEES-exposed corneas exhibited a loss of distinctness of the epithelial-stromal border with frequent dipping into the stroma (also known as pitting). This visible damage, seen in foci throughout the cornea at the epithelial-stromal junction was expected, since this is the known target area of vesicants. In addition, the cells of the anterior stroma were swollen.

CEES-exposed corneas treated with doxycycline in solution have an epithelial-stromal border that appears more normal when compared to those without treatment. The epithelial cell layer demonstrated less pitting, looking more like control tissues. CEES-exposed corneas treated with doxycycline hydrogel were similar to those treated with doxycycline solution, and thus were also much more normal in appearance than CEES-exposed corneas. The flattening of the epithelial-stromal border suggests that these corneas are perhaps more like controls than the CEES-exposed corneas treated with doxycycline solution. CEES causes mild damage, and therefore the difference in corneal wound healing efficacy between doxycycline solution and the doxycycline hydrogel would be expected to be minimal.

Figure 8:
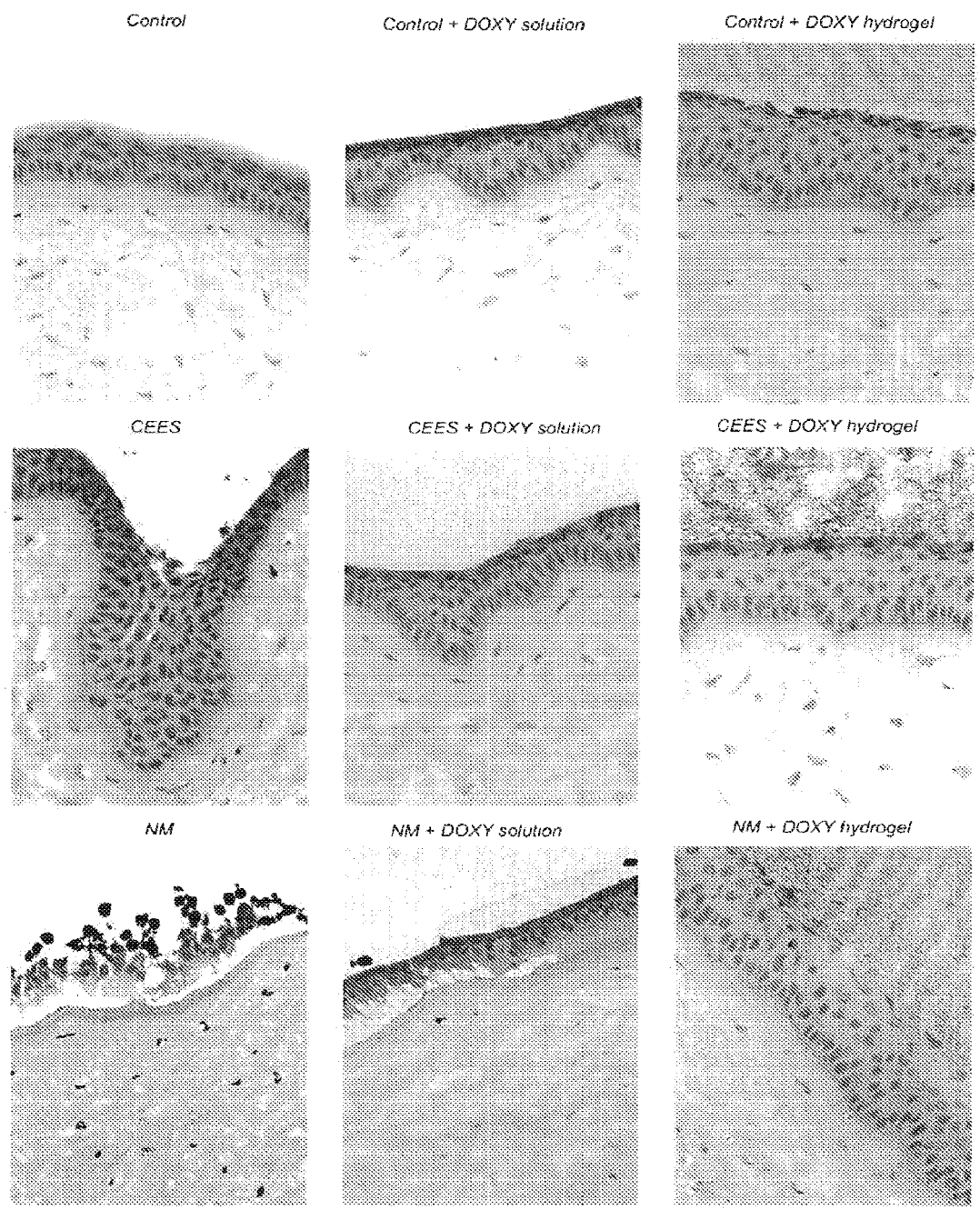
FIG. 8 depicts H & E staining to visualize the histology of CEES and NM-exposed corneas treated for 24 h with doxycycline in solution or in a hydrogel, in which the damaged area is where the epithelium meets the stroma.

The most significant differences that were seen indicated that the hydrogel ameliorated pitting. The micrographs confirm the data from FIG. 8 showing that vesicant exposure damages the cornea and doxycycline treatment acts to maintain the basement membrane zone integrity. Severe damage to the epithelium with NM causes epithelial cell sloughing, epithelial cell dissociation and pitting. The epithelium is detached from the stroma and the epithelial cells are separated, apparently having lost their cell to cell junctions. Where the epithelium is still attached, the basal cell nuclei appear to be more distant from the stroma than in controls.

When treated with doxycycline in solution for 24 h after NM exposure, the epithelial-stromal border is somewhat improved. However there are still many areas where the epithelium is detached from the stroma and in areas where the epithelium and stroma are still attached, the basal cell nuclei were more distant from the stroma than in controls. For NM-exposed samples treated with doxycycline hydrogel, the epithelium remains attached to the basement membrane in most areas and shows a significant improvement in the appearance of the epithelial-stromal border. Doxycycline in solution probably did not show superior efficacy because drop wise application on a curved surface would favor a low retention time and only a small percentage of the doxycycline would be expected to remain in the wound area. The PEG doxycycline hydrogel on the other hand showed a great improvement over the NM exposed corneas.

Example 13—Detection of MMP-9 in Vesicant Exposed and Treated Corneas by Immunofluorescence Phosphate buffer, cross-linker solution, polymers, and hydrogels were prepared as in Example 1.

The sectioned corneas (10 m) were fixed in 100% methanol for 10 min at −20° C. After rinsing with PBS nonspecific binding was blocked with 5% normal goat serum for 1 h. The blocking agent was removed and the sections were incubated with primary mouse anti human MMP-9 monoclonal antibodies (1:400) overnight at 4° C. Sections were blotted and washed four times with PBS/Tween and incubated for 1 h at RT in the dark with Alexa-Fluor 488-conjugated goat anti-mouse IgG secondary antibodies (1:1000). The sections were washed with PBS/Tween, counterstained with DAPI for 5 min, mounted with Prolong gold and cover slipped. Negative controls replaced primary antibodies with PBS. Digital epifluorescent images were captured from a light microscope at 494 nm excitation and 517 nm emission and acquired at 10× magnification.

Figure 9:
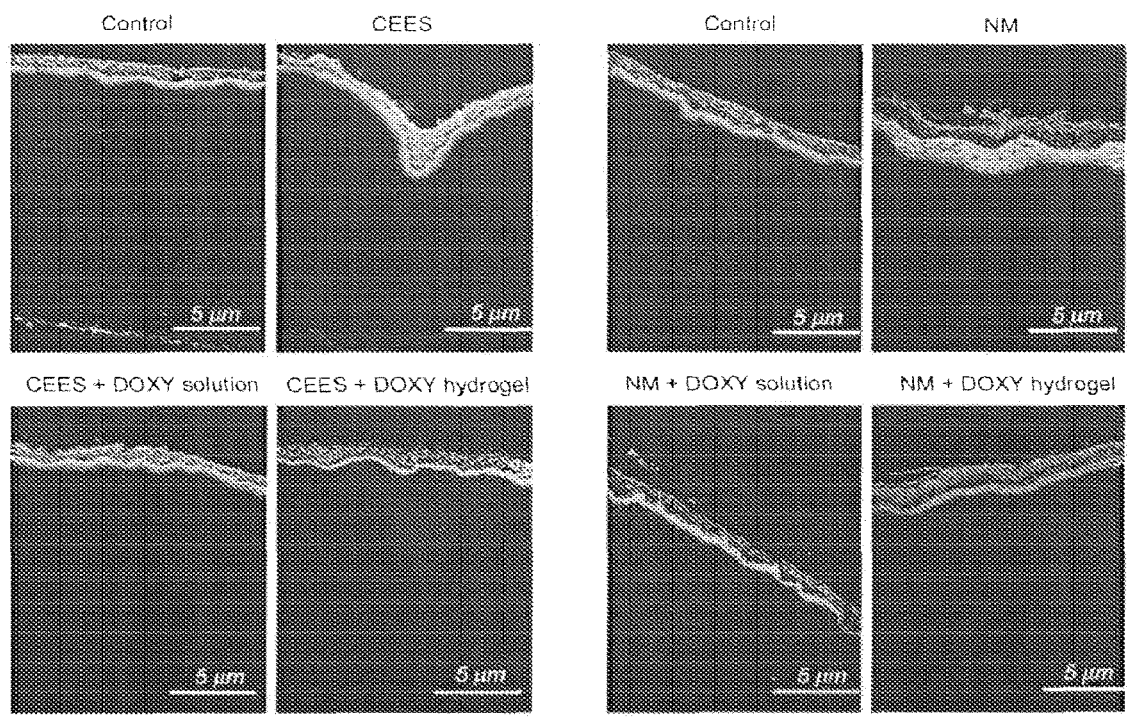
FIG. 9 depicts the immuno-fluorescent staining of corneas exposed to CEES and NM and subsequently treated with doxycycline either in solution or hydrogel.

The IF staining of corneas exposed to CEES and NM, and subsequently treated with doxycycline either in solution or hydrogel for 24 h are shown in FIG. 9. In the controls, a very small amount of MMP-9 staining (green) is seen under the basal epithelial cells in the basement membrane zone. The staining at the apical epithelial cells is typical of the corneal epithelium's auto-fluorescence. Nuclei were stained blue. For CEES exposed corneas, there is a moderate increase in MMP-9 staining observed in the basement membrane zone, apical cells and a small amount throughout the epithelium. For CEES-exposed corneas subsequently treated with doxycycline in solution, there is a slight, if any, decrease in staining. However, applying a doxycycline hydrogel after CEES exposure reduces immuno-reactivity in the basement membrane zone and returning the sub epithelial expression to its original low MMP-9 levels.

For NM-exposed cornea, a drastic increase in MMP-9 staining was observed at the basement membrane zone, reflecting the greater wounding by of NM. The corneas exposed to NM, then treated with doxycycline in solution showed a less intense level of fluorescence. However, in this treatment group, there remained many areas where the epithelial cells were totally detached from the stroma. In this case there were few epithelial cells to secrete MMP-9 and thus there was a lower intensity of fluorescence in those areas. For NM-exposed samples treated with doxycycline hydrogel, the fluorescence was significantly less intense than NM exposure without treatment. Most areas show the epithelium to be in contact with the stroma. Hence intervention of MMP-9 activity with doxycycline hydrogels should be pursued as a potential treatment option for healing of mustard injuries in the eye.

Example 14—Wound Healing Efficacy of Doxycycline PEG Hydrogels on Corneas Exposed to Sulfur Mustered (SM)

Phosphate buffer, cross-linker solution, polymers, and hydrogels were prepared as in Example 1.

Figure 10:
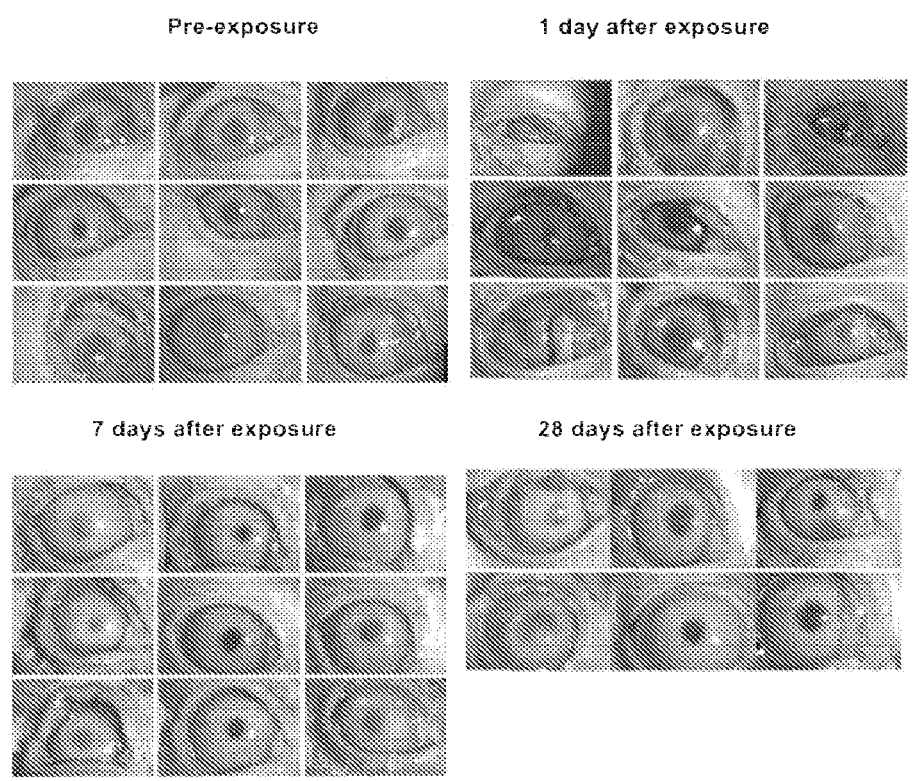
FIG. 10 is a collection of images of rabbit corneas exposed to SM and subsequently treated with doxycycline hydrogel, including pictures of the rabbit cornea after doxycycline hydrogel application.
Figure 11:
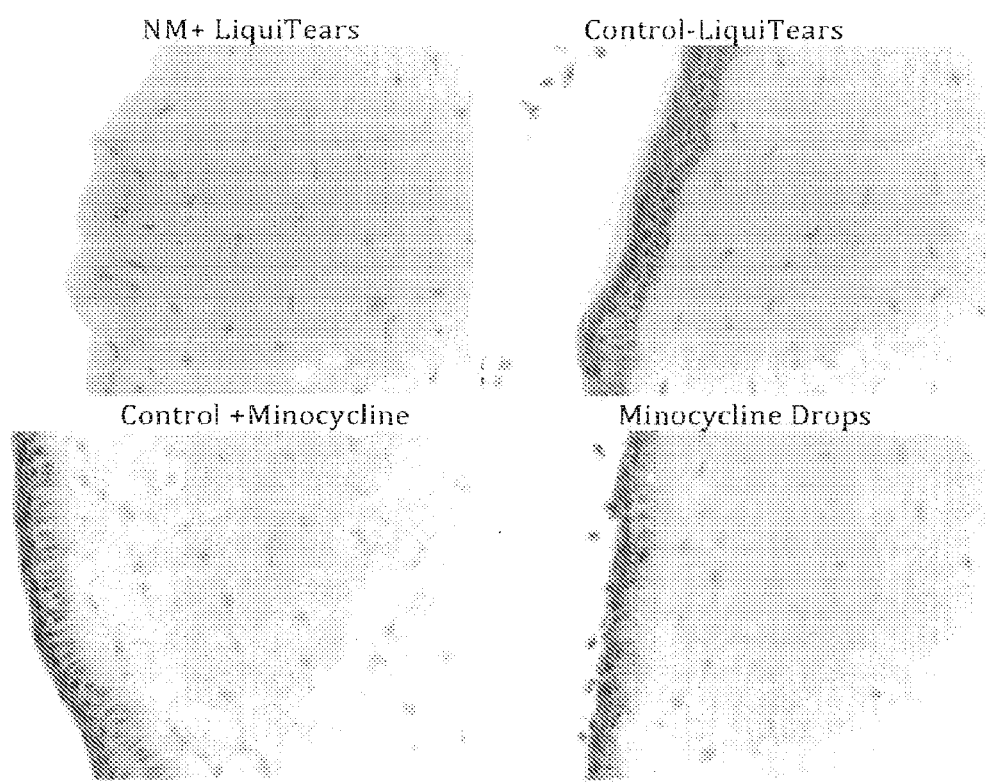
FIG. 11 depicts H & E staining to visualize the histology of NM-exposed corneas treated for 24 h with minocycline drops.

Doxycycline hydrogel (25 µL) solution was applied to the SM exposed rabbit eyes (in the cul de sac). After different time points (1 day, 3 day . . . 28 days) (FIG. 10) the corneas were put in cryomolds containing Tissue-Tek O.C.T. compound with the epithelial side facing down and placed on ice for 15 min before snap freezing them in liquid nitrogen. Corneas were stored at −80° C. until sectioned for histology and immunofluorescence (IF) analysis. The 10 m corneal sections were stained using a modified Hematoxylin & Eosin (H & E) staining method. The corneal sections were fixed in a Pen-Fix solution for 60 s, stained with H & E, dehydrated through graded alcohols, immersed in xylene and covered with a cover slip. Digital images were captured with a light microscope at 40× magnification (FIG. 11). H & E data showed that doxycycline hydrogels improved wound healing efficacy compared to the controls, untreated, doxycycline eye drops and placebo hydrogel treated groups after SM exposure, evidenced by increased survival rates and signs of wound healing.

Example 15—Wound Healing Efficacy of Minocycline Drops on Corneas Exposed to NM

Preparation of Organ Cultures

Eyes arrived from the vendor (Pelfreez, A R) in DMEM+ Penicillin streptomycin, Gentamicin and Amphotericin B. The Corneas were dissected from eyes with about 2-3 mm of scleral rim. Some corneas were directly prepared for frozen sections to serve as controls. Other corneas were prepared for organ culture. These were laid epithelial side down into rounded wells of (Coors) spot plates wetted with a small amount of DMEM medium, then filled with 0.75% agar (Sigma) in 1×DMEM (Gibco). After the agar hardened, the cornea was flipped into a 60 mm glass petri dish (Pyrex), putting the epithelial side up. Medium containing high glucose DMEM, MEM-NEAA, RPMI 1640, Ciprofloxacin and ascorbic acid was applied to the dish up to the corneal-scleral rim. Corneas were allowed to stabilize in the 37° C. culture incubator overnight. During this time, medium was replaced twice. All additions (whether medium, NM and counteragents) were added via pipette onto the central cornea. The following day corneas were for the experimental set up, receiving exposure to NM as a test cornea, or medium as a control.

A. Preparation of Minocycline Drops

Minocycline were prepared as eyedrops at 200 mM concentrations to 1 mg of Minocycline was dissolved in 10 ml teargen ophthalmic solution and vortex for 1 min.

B. Application of Minocycline Drops

Minocycline solution (2M in 50 μL) was added drop wise to the NM exposed central cornea 3 times over the subsequent 24 h. After 24 h, the corneas were put in cryomolds containing Tissue-Tek O.C.T. compound with the epithelial side facing down and placed on ice for 15 min before snap freezing them in liquid nitrogen. Corneas were stored at −80° C. until sectioned for histology and immunofluorescence (IF) analysis. The 10 m corneal sections were stained using a modified Hematoxylin & Eosin (H & E) staining method. The corneal sections were fixed in a Pen-Fix solution for 60 s, stained with H & E, dehydrated through graded alcohols, immersed in xylene and covered with a cover slip. Digital images were captured with a light microscope at 40× magnification (FIG. 11).

Example 16—Wound Healing of Minocycline PEG Hydrogels on Corneas Exposed to NM

Phosphate buffer, cross-linker solution, polymers, and hydrogels were prepared as in Example 1.

A. Wound Healing Efficacy of Minocycline PEG Hydrogels

The procedure for the preparation of phosphate buffer, and NM exposure was used as it is, as mentioned in example 3.

B. Application of Minocycline Hydrogels on NM Exposed Central Cornea

Figure 12:
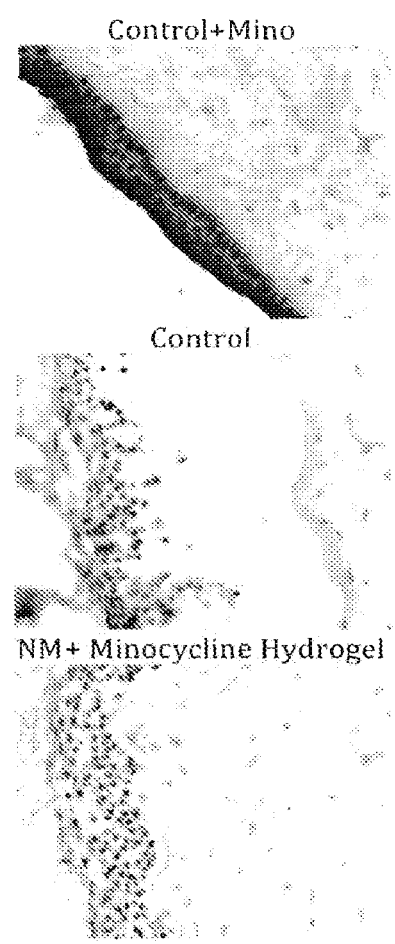
FIG. 12 depicts H & E staining to visualize the histology of NM-exposed corneas treated for 24 h with minocycline PEG hydrogel.

Minocycline hydrogel (200 μL) solution was applied drop wise to the NM exposed central cornea. After 24 h the corneas were put in cryomolds containing Tissue-Tek O.C.T. compound with the epithelial side facing down and placed on ice for 15 min before snap freezing them in liquid nitrogen. Corneas were stored at −80° C. until sectioned for histology and immunofluorescence (IF) analysis. The 10 m corneal sections were stained using a modified Hematoxylin & Eosin (H & E) staining method. The corneal sections were fixed in a Pen-Fix solution for 60 s, stained with H & E, dehydrated through graded alcohols, immersed in xylene and covered with a cover slip. Digital images were captured with a light microscope at 40× magnification (FIG. 12).

Example 17—Wound Healing Efficacy of NDH4417 Drug Drops on Corneas Exposed to NM Phosphate buffer preparation, NM exposure and preparation of organ cultures was performed as in example 13.

A. Preparation of NDH-4417 Drops

NDH4417 were prepared as eye drops at 200 μL concentration. 0.62 mg of NDH 4417 was dissolved in 50 ul DMSO (final concentration of 0.5%, maximum amount okay for cells). The dissolved compound in DMSO was vortexed and coated around the vial. 10 ml Teargen ophthalmic solution was added rapidly via pipette while vortexing.

B. Application of NDH4417 Drops

Figure 13:
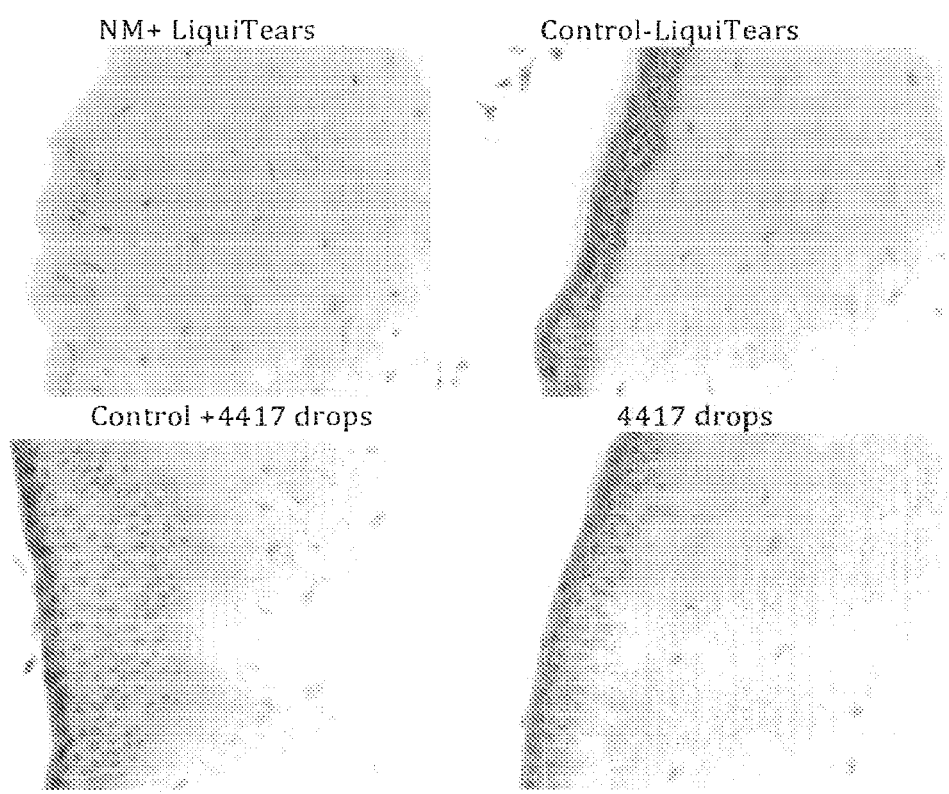
FIG. 13 depicts H & E staining to visualize the histology of NM-exposed corneas treated for 24 h with NDH4417 drops.

Drug solution (2M in 50 μL) was added drop wise to the NM exposed central cornea three times over the subsequent 24 h. After 24 h, the corneas were put in cryomolds containing Tissue-Tek O.C.T. compound with the epithelial side facing down and placed on ice for 15 min before snap freezing them in liquid nitrogen. Corneas were stored at −80° C. until sectioned for histology and immunofluorescence (IF) analysis. The 10 m corneal sections were stained using a modified Hematoxylin & Eosin (H & E) staining method. The corneal sections were fixed in a Pen-Fix solution for 60 s, stained with H & E, dehydrated through graded alcohols, immersed in xylene and covered with a cover slip. Digital images were captured with a light microscope at 40× magnification (FIG. 13).

Example 18—Wound Healing of Olvanil RetroOH-8 (NDH-4417) Drugs PEG Hydrogels on Corneas Exposed to NM Phosphate buffer, cross-linker solution, polymers, and hydrogels were prepared as in Example 1 and as in example 13.

A. Preparation of Drug Solution

NDH4417 (8.5 mg) was dissolved in 250 μL DMSO (final concentration of 0.5%, maximum amount okay for cells).

B. Preparation of Hydrogel (0.2 mL)

The polymer solution (100 μL) containing the nanocarrier was transferred to a glass vial (12×32 mm, SepCap clear vial, Catalog # C4011-80, National Scientific Company, Rockwood, Tenn.) followed by drug solution (1 μL). The cross-linker solution (99 μL) was transferred to a polymer and drug solution. The solution mixture was allowed to stand at room temperature (24° C.). The hydrogel solution started becoming more and more viscous after 25 Sec and ceased to flow from the inverted tube in 45 Sec indicating the formation of hydrogel.

C. Application of NDH4417 Hydrogels on NM Exposed Central Cornea

Figure 14:
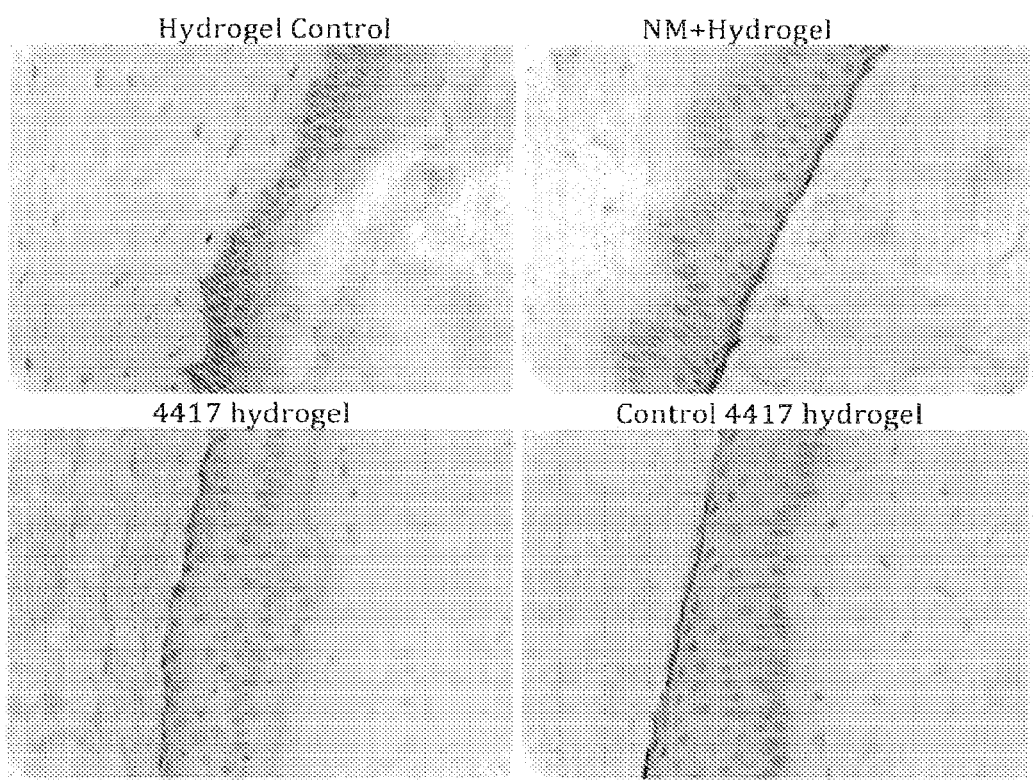
FIG. 14 depicts H & E staining to visualize the histology of NM-exposed corneas treated for 24 h with NDH4417 PEG hydrogel.

NDH4417 hydrogel (200 μL) was applied to the NM exposed central cornea. After 24 h the corneas were put in cryomolds containing Tissue-Tek O.C.T. compound with the epithelial side facing down and placed on ice for 15 min before snap freezing them in liquid nitrogen. Corneas were stored at −80° C. until sectioned for histology and immunofluorescence (IF) analysis. The 10 m corneal sections were stained using a modified Hematoxylin & Eosin (H & E) staining method. The corneal sections were fixed in a Pen-Fix solution for 60 s, stained with H & E, dehydrated through graded alcohols, immersed in xylene and covered with a cover slip. Digital images were captured with a light microscope at 40× magnification (FIG. 14).

Example 19—Minocycline PEG Additive Hydrogels for Mice Back Model

Phosphate buffer, cross-linker solution, polymers, and hydrogels were prepared as in Example 3

A. Preparation of Hydrogel (0.2 mL)

The cross-linker solution (100 μL) containing nanocarrier (0.25% minocycline) was transferred to a glass vial (12×32 mm, SepCap clear vial, Catalog # C4011-80, National Scientific Company, Rockwood, Tenn.), followed by polymer solution (100 μL) containing additives 5% v/v glycerin, 4% w/v PVP and 5% v/v PEG 600. The solution mixture was allowed to stand at room temperature (24° C.). The hydrogel solution started becoming more and more viscous after 30 Sec and ceased to flow from the inverted tube in 48 Sec indicating the formation of hydrogel.

Figure 15:
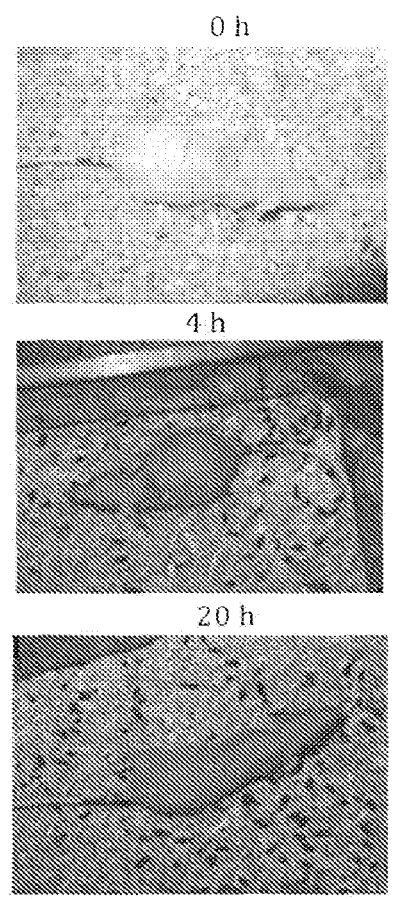
FIG. 15 provides photos of mice treated with minocycline hydrogel (0 h, 4 h and 20 h) applied to skin.

Hydrogel solution was applied on the back of the SKH-1 mice after 30 sec (once solution is viscous). It was observed that after 4 h hydrogel stays on the skin (FIG. 15). After 20 h it was observed hydrogel disappears.

Example 20—Dose and Time Dependent Effects of NM on Mouse Skin

A SKH-1 hairless mouse model was used to assess NM dermal wound progression in vivo. NM dissolved in acetone was applied topically to the dorsal skin of mice and left in the hood overnight to degas. A standard circular template (15 mm) was used to ensure uniform exposure area of NM on all mice. For the dose response study, topical wounds were created by application of 5, 25, 50, 75 and 100 μmoles NM. The mice were euthanized by $CO_2$ gas and punch biopsies were collected at 24 h after exposure to evaluate the dose dependent effects of NM on dermal wound formation. The dose of NM at which a lesion forms and mice survive for at least 168 h was chosen for time response, inflammatory biomarkers and permeation studies. For the time response study, topical wounds were created by application of 5 μmoles of NM (which was based on the results of the dose response study) and punch biopsies were collected from the wounded skin at 0, 24, 72 and 168 h. The skin samples were fixed in 10% formalin and histology evaluated by H&E staining. Both the dose and time response treatments included five mice in each group.

Figure 16:
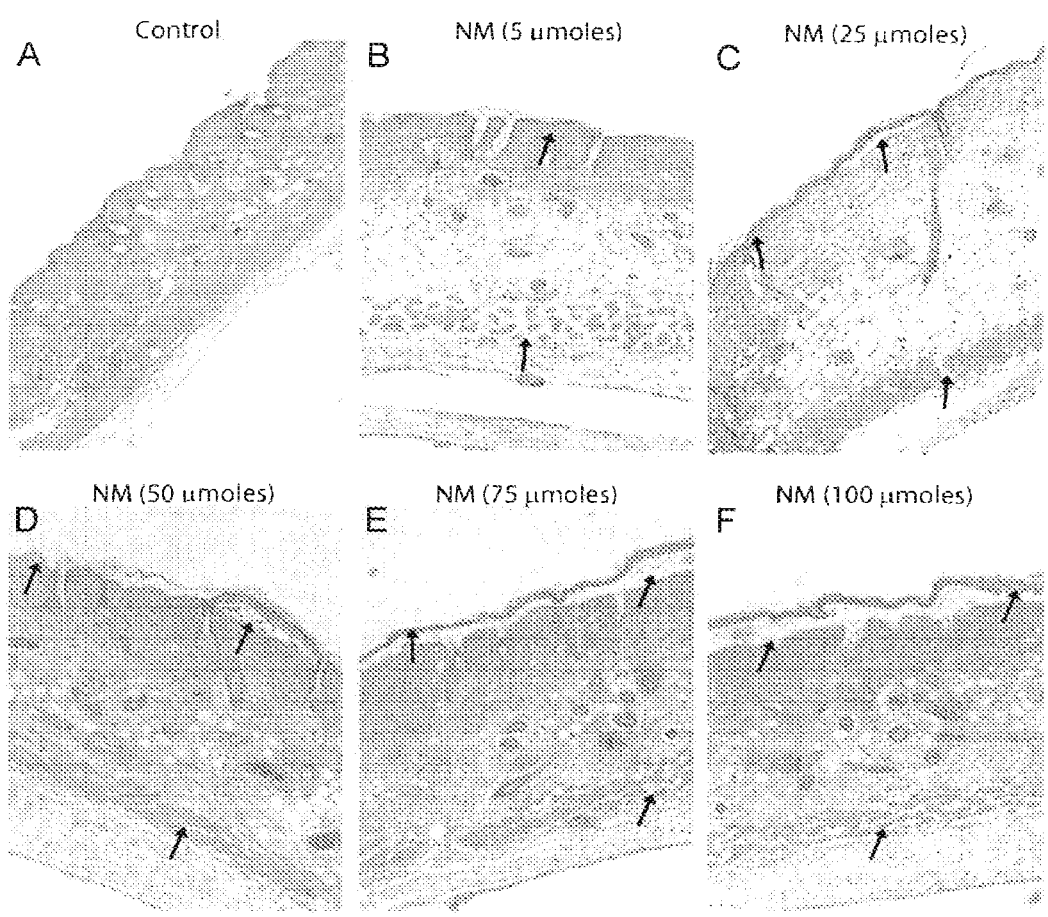
FIG. 16 depicts H & E staining to visualize the histology of dose dependent effects of NM exposure on mouse skin.
Figure 17:
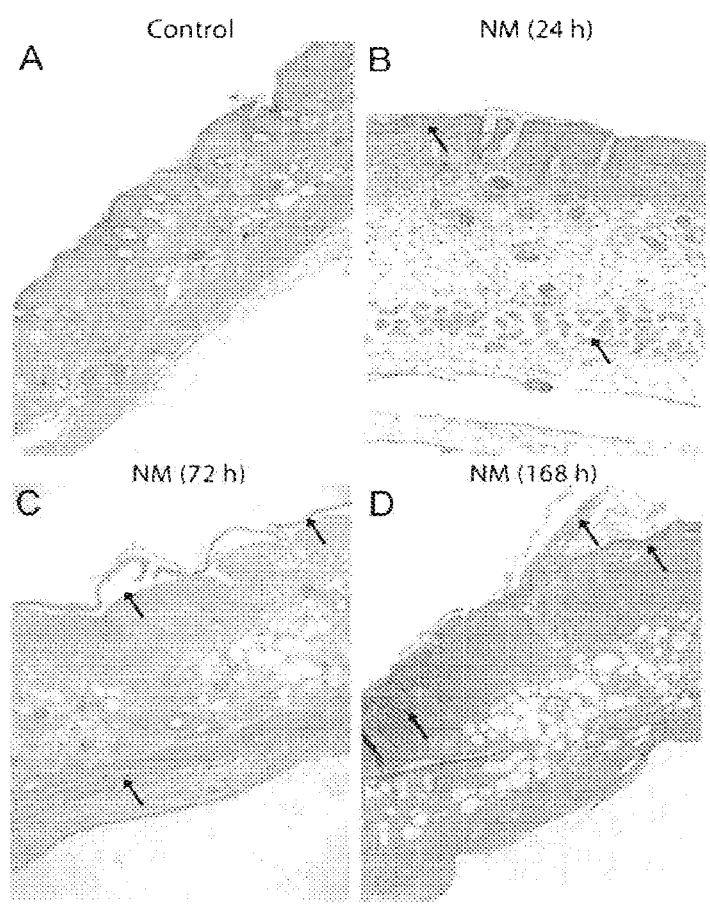
FIG. 17 depicts H & E staining to visualize the histology of time dependent effects of NM exposure on mouse skin.

Histology of NM exposed mouse skin indicated a dose and time dependent wound progression (FIGS. 16 and 17). A dose dependent investigation was conducted at 24 h after NM administration (FIG. 16). All mice exposed to NM at doses higher than 5 μmoles survived for less than a week demonstrating that NM is extremely toxic when applied topically. NM induced wound progression was monitored for upto 168 h after exposure (FIG. 17). Histology of skin samples obtained 24 h after NM exposure, mainly showed edema, pyknotic nuclei in the epidermis, inflammatory infiltration and discontinuity of the skeletal muscle. Indeed, in FIG. 16, which provides histological slides illustrating the dose dependent effects of NM exposure on mouse skin visualized by H & E staining (10×), the arrows in B denote pyknotic nuclei in epidermis and discontinuous skeletal muscle in the dermis. Arrows in C, D, E and F denote pyknotic nuclei in epidermis, separation of epidermis from dermis and discontinuous skeletal muscle in dermis. The separation of epidermis from the dermis progresses in a dose dependent manner from 5-100 μmoles. In FIG. 17, the arrows in B denote pyknotic nuclei in epidermis and discontinuous skeletal muscle in the dermis. Arrows in C denote absence of nuclear staining in the epidermis, separation of epidermis from dermis and discontinuous skeletal muscle in dermis. Arrows in D denote dermal necrosis with, reepithelization from the wound edges characterized by epidermal hyperplasia and hyperkeratosis.

In the skin samples obtained 72 h after NM exposure, edema, separation of the epidermis from the dermis, death of the epidermal cells (no nuclear staining) and discontinuity of the skeletal muscle was observed. At 168 h after NM exposure, reepithelization in the epidermis (a sign of wound healing) from the wound edges was observed along with necrosis in the dermis. The results of the time response study indicate that the NM (5 μmoles) induced wound progresses from 0-72 h and wound healing initiates between 72-168 h in SKH-1 mice.

Example 21—Determine the Significance of NM Exposure Time on Edema

Figure 18:
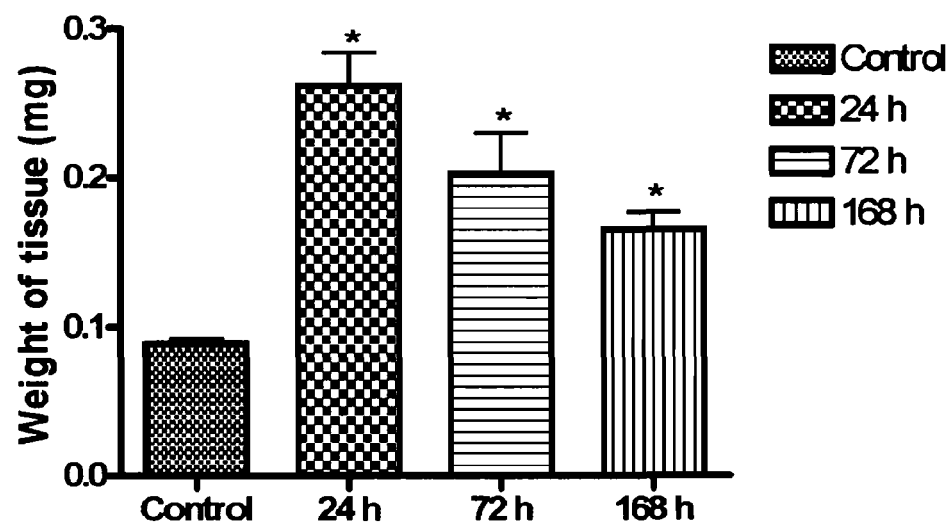
FIG. 18 demonstrates marked edema overtime when mouse skin is exposed to NM.

Punch biopsies from the dorsal wounded skin of mice were collected at 0, 24, 72 and 168 h. The weight of the tissue was measured and the results were reported as mean±SEM of five mice in each treatment group. One-way analysis of variance (ANOVA) was used to determine the significance of NM exposure time on edema. The tissue weight of biopsy from NM exposed skin was measured to determine the extent of edema. FIG. 18 indicates that dermal edema is dependent on the duration of NM exposure. A significant increase ($p<0.05$) in tissue weight compared to the control was observed at 24, 72 and 168 h after exposure to NM, demonstrating marked edema in a time dependent manner, with edema being highest at 24 h.

Example 22—Determine the Significance of NM Exposure Time on mRNA Levels of the Inflammatory Biomarkers IL-10 and TNF-α

The punch biopsy samples from the wounded skin of mice collected at 0, 24, 72 and 168 h were snap frozen in liquid nitrogen and stored at −80° C. until further analysis of RNA. The results were reported as mean±SEM of five mice in each treatment group. One way ANOVA was used to determine the significance of NM exposure time on mRNA levels of the inflammatory biomarkers IL-1β and TNF-α.

The RNA isolation and reverse transcription were performed using methods known in the art. Briefly, total RNA was isolated from the tissue samples using TRIzol reagent, according to the manufacturer's instructions. Eppendorf phase lock gel, a product that eliminates interface-protein contamination during phenol extraction and was added during centrifugation. The RNA pellet was dissolved in RNA storage solution and RNA quantitated spectrophometrically at 260 nm. Total RNA (1 µg) was reverse-transcribed into cDNA using a High Capacity cDNA Reverse Transcription Kit for reverse transcriptase-polymerase chain reaction (RT-PCR). A minus reverse transcriptase reaction was used as a control.

The mRNA levels of IL-1β and TNF-α were measured from cDNA samples by TaqMan gene expression assay. To compensate for variations in input RNA amounts, and efficiency of reverse transcription, GAPDH an endogenous control gene was also quantified, and results were normalized to these values.

Figure 19:
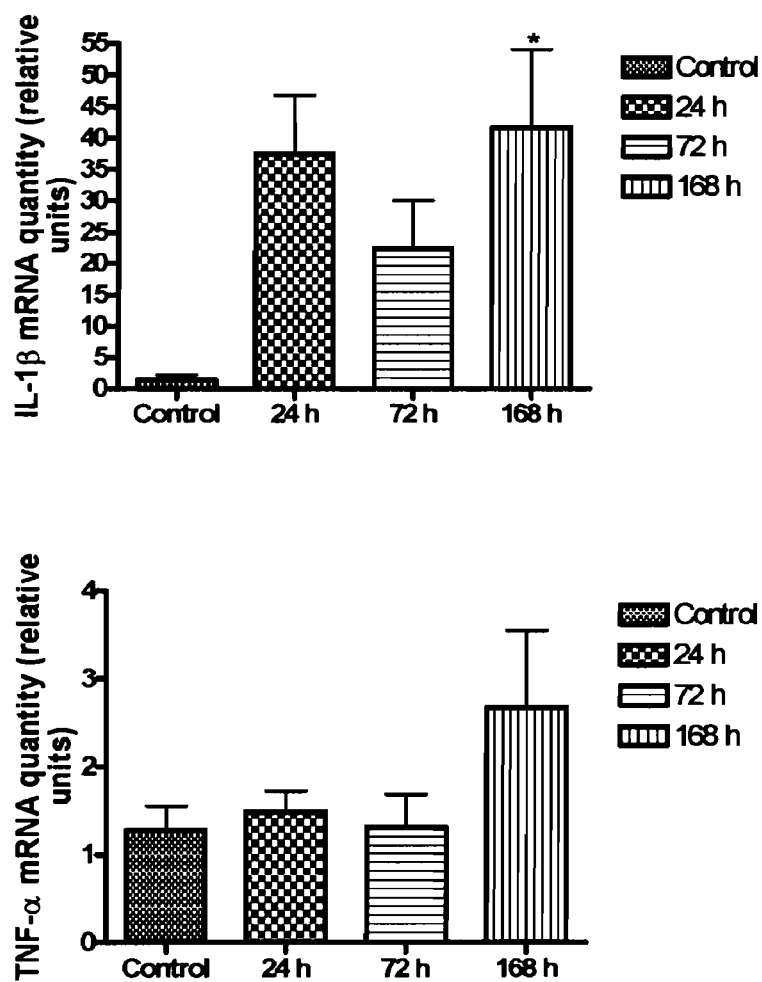
FIG. 19 demonstrates increased mRNA expression levels of both IL-1β and TNF-α at 24, 72 and 168 h after exposure to NM on mouse skin.

FIG. 19 shows the mRNA levels of IL-1β and TNF-α in NM exposed skin. The mRNA levels of both the inflammatory markers increased at 24, 72 and 168 h after NM exposure relative to control skin, with peak activity at 168 h. Only the mRNA levels of IL-1β at 168 h after NM exposure were found to be significantly higher than the control ($p<0.05$).

Example 23—Measurement of Permeability of Molecular Markers Through NM Exposed Skin The damage caused by vesicant exposure on the integrity and barrier properties of skin was evaluated by measuring skin permeability, at various time points following NM exposure. [3H] mannitol (molecular weight=182.17) was used as a hydrophilic marker; FD-4, FD-10, FD-20 and FD-40 were used as molecular weight markers; Rhodamine 123 (molecular weight=380.82) was used as a lipophilic marker. The permeability profiles were evaluated on mice skin collected at 0 (controls), 24, 72 and 168 h after exposure to NM.

Figure 20:
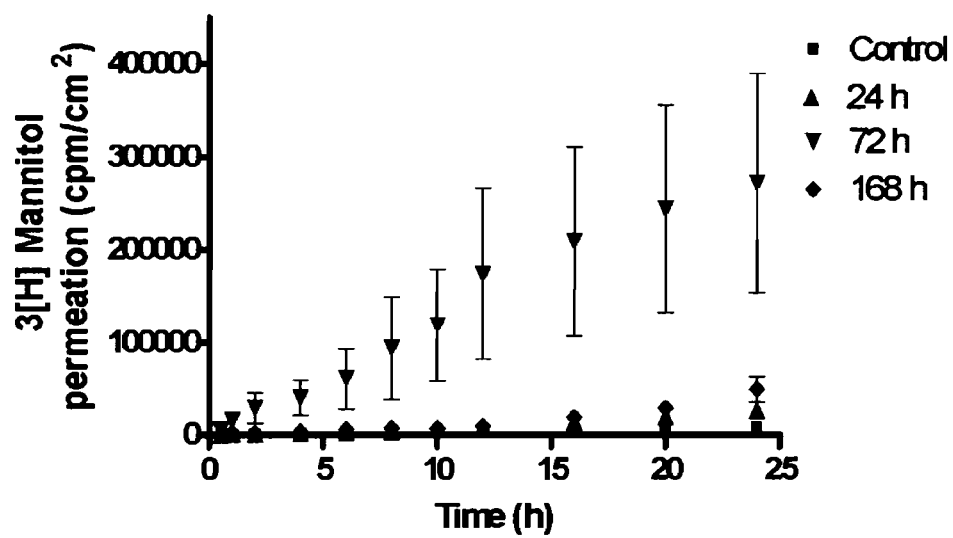
FIG. 20 demonstrates the permeation profile of 3[H] mannitol through NM exposed mouse skin.
Figure 21:
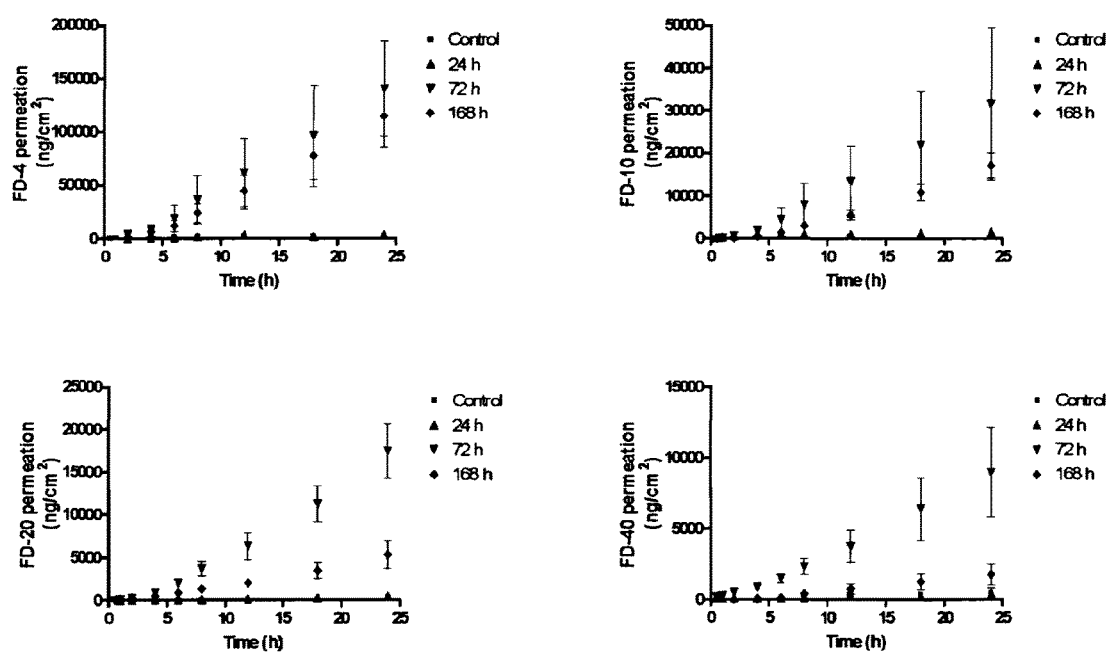
FIG. 21 demonstrates the permeation profile of FITC-dextran's through NM exposed mouse skin.
Figure 22:
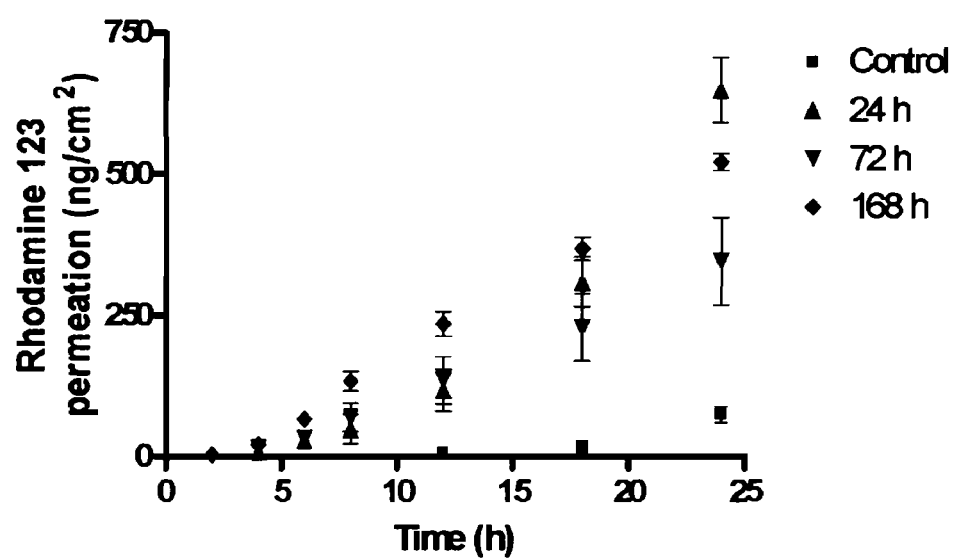
FIG. 22 demonstrates the permeation profile of rhodamine 123 through NM exposed mouse skin.

Permeability studies were carried out using a Franz diffusion cell apparatus (diameter of 5 mm and diffusional area of 0.636 $cm^2$) as previously described by Anumolu et al. (Anumolu et al., 2009). Mouse skin was excised and placed in PBS (Phosphate buffered saline, pH 7.4) for 1 h prior to being sandwiched between the lower cell reservoir and the glass cell-top. The receiving compartment (volume 5.1 mL) was filled with PBS and the medium was continuously stirred (600 rpm) with a magnetic bar to avoid stagnant aqueous diffusion layer effects. The system was maintained at 37° C. using a circulating water bath and a jacket surrounding the cell. 200 µL of each marker in PBS was placed in the donor compartment, which was then sealed with parafilm and aluminum foil to prevent evaporation. Aliquots (200 µL) were withdrawn from the receiver compartment at predetermined intervals and replaced with equal volume of PBS to maintain sink conditions through out the study. The specific activity of [3H] mannitol permeated was measured with a LSC. The amounts of FD-4, FD-10, FD-20, FD-40 and rhodamine 123 markers that permeated through the skin samples were measured using a fluorescent plate reader (Ex=485 nm; Em=520 nm). All permeability studies were conducted in triplicate and the results were reported as the mean±SEM. Student's t-test was used to determine the effect of NM exposure time on the permeation of molecular markers. FIGS. 20, 21 and 22 show the cumulative amount of molecular marker permeated ($cpm/cm^2$ or $ng/cm^2$) as a function of time (h).

The permeation of the hydrophilic marker 3[H] mannitol increased significantly through mice skin exposed to NM for various time periods compared to the control (FIG. 20 which provides the permeation profile of 3[H] mannitol (hydrophilic marker) through NM exposed mouse skin.). The order of permeation of mannitol is 72 h>168 h>24 h>control (table 6). The effect of molecular weight on permeability through intact and NM damaged skin was studied using different molecular weight markers of FITC-dextran's (FIG. 21). Irrespective of their molecular weight, the FITC-dextran's, at all time points post NM exposure exhibited a significant increase in permeation compared to control skin (Table 6). The order of permeation of FD-4, FD-10, FD-20 and FD-40 is 72 h>168 h>24 h>control. The permeability coefficients of FITC dextran's through control and NM exposed skin declined with increasing molecular weight (FD-4>FD-10>FD-20>FD-40) demonstrating that permeability through skin is molecular weight dependent. The permeability of rhodamine 123 through control skin is much higher than that of the other molecular markers evaluated in the current study. The order of permeation of the lipophilic marker rhodamine 123 through NM exposed skin is 24 h>168 h>72 h>control (FIG. 22). All the molecular markers showed an increased permeation through NM exposed skin compared to the control, which demonstrates that the barrier property is compromised in vesicant exposed skin.

TABLE 6

Permeability coefficients of different molecular markers through skin exposed to NM for 0, 24, 72 and 168 h

| | Permeability coefficient (cm · $h^{-1}$) × $10^{-6}$ | | | |
|---|---|---|---|---|
| Molecular marker | Control (No NM exposure) | 24 h after NM exposure | 72 h after NM exposure | 168 h after NM exposure |
| 3[H] mannitol | 27.45 ± 2.47 | 96.36 ± 13.68 | 1091 ± 216 | 157.7 ± 18.6 |
| Rhodamine 123 | 161.5 ± 75.58 | 889.7 ± 124.4 | 477.1 ± 14.14 | 692.2 ± 18.32 |
| FD-4 | 15.23 ± 1.76 | 28.55 ± 9.38 | 1270 ± 43.21 | 1054 ± 42.03 |
| FD-10 | 5.06 ± 0.54 | 9.52 ± 1.40 | 278.7 ± 10.18 | 157.2 ± 9.85 |
| FD-20 | 1.84 ± 0.15 | 3.15 ± 0.34 | 147 ± 8.53 | 43.82 ± 2.34 |
| FD-40 | 1.67 ± 0.56 | 2.60 ± 0.38 | 75 ± 28.72 | 16.61 ± 0.66 |

What is claimed is:

1. A method of treating the skin or eyes of a mammal exposed to a vesicant compound comprising administering to said exposed skin or eyes of said mammal a formulation consisting essentially of an active ingredient consisting of doxycycline, minocycline, or a mixture thereof; a linear or branched cross-linkable PEG having from 2 to 8 arms, said PEG derivatized with —SH; and (A) a cross-linker containing two or more thio-reactive group independently selected from pyridyldithio, N-Hydroxysuccinimide (NHS), vinylsulfone and maleimide; or (B) an oxidizing agent;

wherein said at least one of doxycycline and minocycline is uncoupled or coupled to said PEG through degradable bonds.

2. The method of claim 1, wherein said vesicant compound is selected from the group consisting of sulfur mustard (SM), nitrogen mustard (NM) and half mustard (2-chloroethyl ethyl sulfide (CEES)).

3. The method of claim 1, wherein said formulation administered in a form of an ocular formulation to an eye of said mammal.

4. The method of claim 3, wherein said ocular formulation is fabricated as a contact lens.

5. The method of claim 1, wherein said formulation is administered in a form of a topical formulation to a portion of said mammal skin exposed to said vesicant compound.

6. The method of claim 1, wherein said oxidizing agent is hydrogen peroxide.

7. The method of claim 1, wherein the concentration of said at least one of doxycycline or minocycline is 0.1-12% (w/v).

8. The method of claim 1, wherein the at least one of doxycycline or minocycline is uncoupled to said PEG.

9. The method of claim 1, wherein the at least one of doxycycline or minocycline is coupled to the polymer through degradable bonds.

10. The method of claim 1, wherein said degradable bonds are enzyme-sensitive peptide linker bonds, self-immolative linker bonds, acid and base-sensitive linker bonds, pH sensitive linker bonds, multifunctional organic linking agent bonds, multifunctional inorganic crosslinking agent bonds or peptidic backbone bonds.

11. The method of claim 10, wherein said peptidic backbone bonds contain a sequence $CH_3CO$—$(X—Z—Z)_x$—$(Y—Z—Z)_y$—$CONH_2$, where X=Lys, Glu, Asp or diaminobutyric acid; Y=Cys, homocysteine or 1-amino-2-methyl-2-propanethiol; Z=β-Ala, Gly, Ala, or GABA (gamma-amino butyric acid); x and y are interchangeable; x is between 1 to 4; y is between 1 to 4; minimum number of Z-spacer on the peptide backbone=2; maximum number of Z-spacer on the peptide backbone=4.

12. The method of claim 10, wherein said peptide linker bonds comprise at least one of Leu-Gly, $Glu(Leu-Gly)_2$, Arg-Gly-Asp, Arg-Gly-Asp-Cys, Gly-Arg-Gly-Asp-Ser, Gly-Arg-Gly-Asp-Ser-Pro, or cyclic Arg-Gly-Asp-Tyr-Lys.

13. The method of claim 1, wherein the at least one of doxycycline or minocycline is bound to a targeting moiety.

14. The method of claim 13, wherein the targeting moiety is a peptide.

15. The method of claim 14, wherein said peptide is selected from the group consisting of an RGD peptide, EGF peptide, DV3 (LGASWHRPDKC) peptide, a LYP peptide (CGNKRTRGC), membrane-binding domain of IGFBP3 (QCRPSKGRKRGFCW), fMLF, mannose, transferrin ligand, and monoclonal antibodies.

* * * * *